(12) United States Patent
Bornzin et al.

(10) Patent No.: US 9,586,039 B2
(45) Date of Patent: Mar. 7, 2017

(54) NEUROSTIMULATION LEADS HAVING NON-PLANAR CONTOURS AND METHODS INCLUDING THE SAME

(71) Applicant: PACESETTER, INC., Sylmar, CA (US)

(72) Inventors: Gene A. Bornzin, Simi Valley, CA (US); Lalit Venkatesan, Prosper, TX (US)

(73) Assignee: PACESETTER, INC., Sylmar, CA (US)

( * ) Notice: Subject to any disclaimer, the term of this patent is extended or adjusted under 35 U.S.C. 154(b) by 240 days.

(21) Appl. No.: 14/201,204

(22) Filed: Mar. 7, 2014

(65) Prior Publication Data

US 2015/0251003 A1  Sep. 10, 2015

(51) Int. Cl.
*A61N 1/05* (2006.01)
*A61B 5/055* (2006.01)

(52) U.S. Cl.
CPC .............. *A61N 1/0531* (2013.01); *A61B 5/055* (2013.01); *A61B 2576/026* (2013.01); *A61N 1/0553* (2013.01)

(58) Field of Classification Search
CPC .. A61N 1/0526; A61N 1/0529; A61N 1/0531; A61N 1/0534; A61N 1/0553
USPC ............................................ 607/115–116, 45
See application file for complete search history.

(56) References Cited

U.S. PATENT DOCUMENTS

| | | | |
|---|---|---|---|
| 2004/0243208 A1* | 12/2004 | Jordan | A61N 1/0553 607/117 |
| 2010/0070010 A1* | 3/2010 | Simpson | A61N 1/0553 607/117 |
| 2012/0283808 A1* | 11/2012 | Swanson | A61N 1/0553 607/117 |

* cited by examiner

*Primary Examiner* — Paula J Stice

(57) ABSTRACT

A neurostimulation (NS) lead configured to provide NS therapy to nervous tissue. The NS lead includes a lead body having an active side and a posterior side that face in generally opposite directions. The NS lead includes an array of electrodes provided on the active side and configured to face the nervous tissue and provide the NS therapy to the nervous tissue. The NS lead also includes a non-planar contour formed in the active side. The non-planar contour includes a plurality of slopes that form a morphological feature. The morphological feature is one of a projection or a depression that extends along a designated path on the active side.

10 Claims, 11 Drawing Sheets

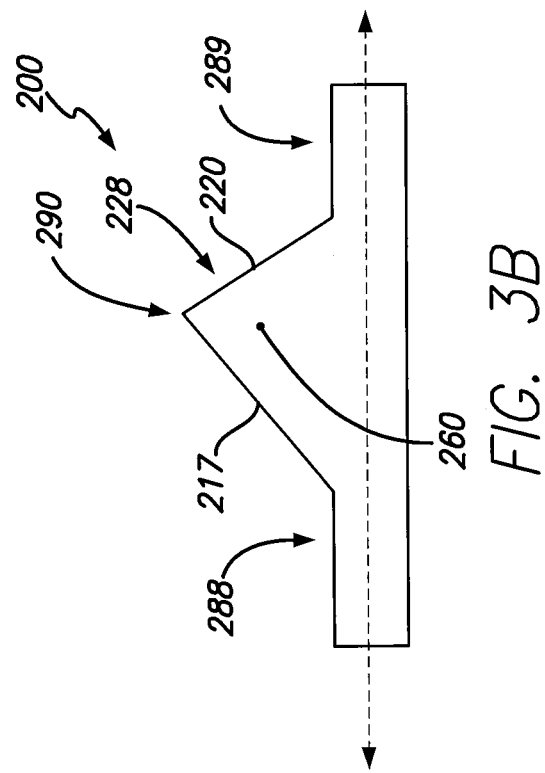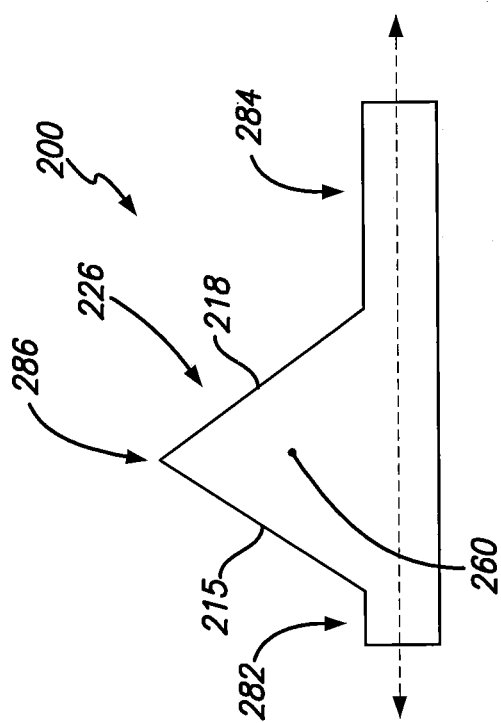

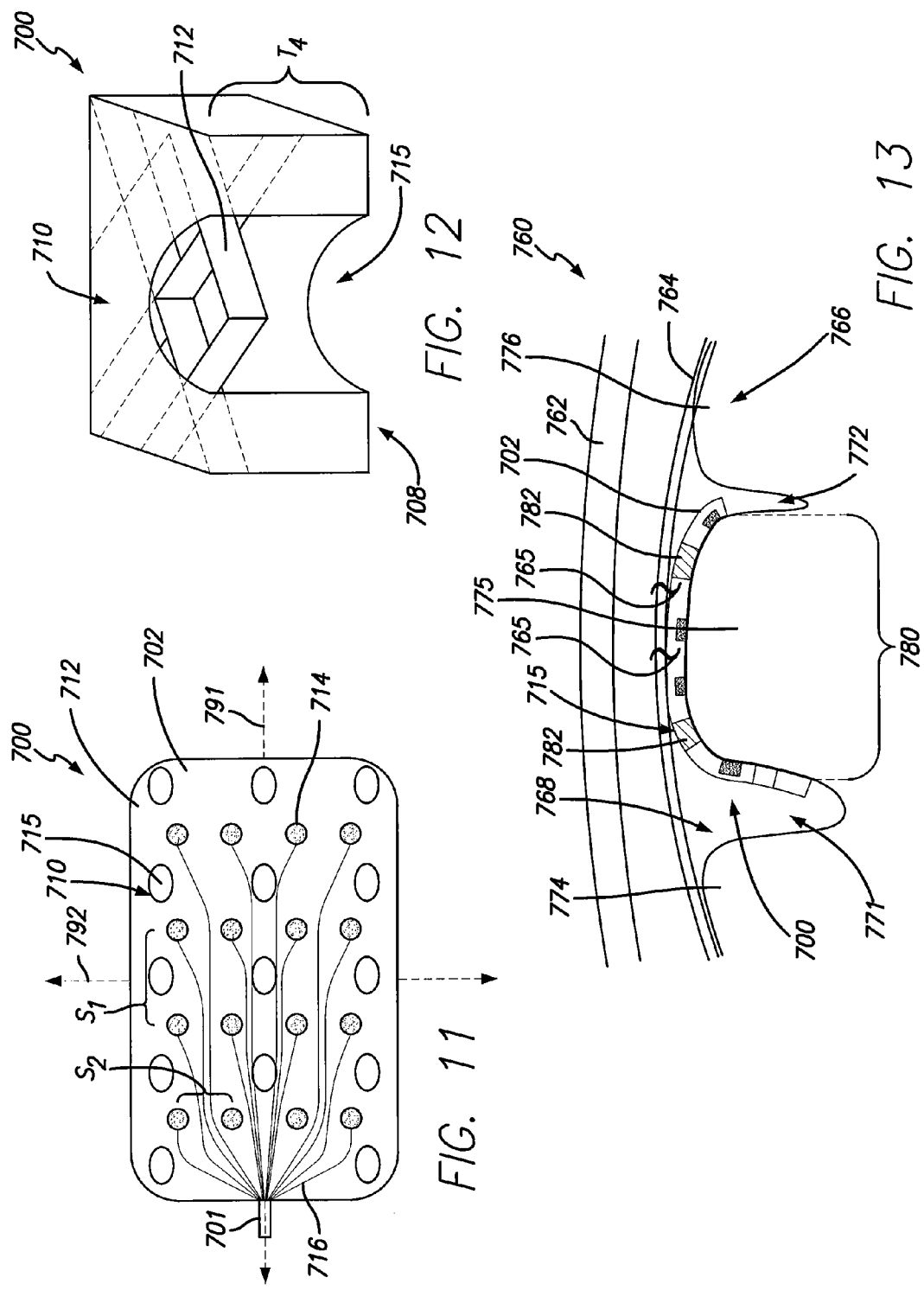

NEUROSTIMULATION LEADS HAVING NON-PLANAR CONTOURS AND METHODS INCLUDING THE SAME

FIELD OF THE INVENTION

One or more embodiments of the subject matter described herein generally relate to apparatuses or methods for generating electrical fields proximate to nervous tissue.

BACKGROUND OF THE INVENTION

Neurostimulation systems (NS) include NS leads that generate electrical pulses and deliver the pulses to nervous tissue to treat a variety of disorders. The NS lead typically includes a lead body having a number of electrodes that directly or indirectly engage with the nervous tissue. The electrodes have a predetermined arrangement (e.g., linear series or a two-dimensional array) and are controlled by a pulse generator of the NS system that may be implanted within the individual. For example, cortical stimulation (CS) is a relatively new modality that has been used in the management of movement disorders (e.g., Parkinson's disease, essential tremor, dystonia, and movement dysfunction due to a cortical infarct), psychological disorders (e.g., treatment-resistant depression), and pain that is resistant to other treatments. Another modality, peripheral nerve stimulation (PNS), has been used to treat chronic migraines and headaches. Spinal cord stimulation (SCS) has been used to manage pain, among other things.

The NS lead is typically positioned at a target site along the nervous tissue during surgery. The therapy delivered by the electrodes may be based on the different positions of the electrodes relative to one another and the nervous tissue. One challenge for NS leads, including those NS leads used for CS, PNS, and SCS, is migration of the NS lead from the original target site. More specifically, through time, the NS leads may shift from the original target site causing the electrodes to have different positions with respect to the nervous tissue. This may result in adverse events or a decrease in an effectiveness of the therapy. In some cases, it may be necessary to have an additional surgery for re-positioning the NS lead. Repeated surgeries may result in patient dissatisfaction and a removal of the entire NS system.

Accordingly, there is a need for NS leads, systems, and methods that reduce the likelihood of lead migration after an NS lead has been positioned at a target site.

BRIEF SUMMARY

In an embodiment, a neurostimulation (NS) lead configured to provide NS therapy to nervous tissue is provided. The NS lead includes a lead body having an active side and a posterior side that face in generally opposite directions. The NS lead includes an array of electrodes provided on the active side and configured to face the nervous tissue and provide the NS therapy to the nervous tissue. The NS lead also includes a non-planar contour formed in the active side. The non-planar contour includes a plurality of slopes that form a morphological feature. The morphological feature is one of a projection or a depression that extends along a designated path on the active side.

In an embodiment, a neurostimulation (NS) lead configured to provide NS therapy to nervous tissue is provided. The NS lead includes a lead body having an active side and a posterior side that face in generally opposite directions. The active side has an array of electrodes that are configured to face the nervous tissue and provide the NS therapy to the nervous tissue. The active side has a non-planar contour that includes a plurality of slopes forming a morphological feature. The morphological feature is one of a projection or a depression that extends along a designated path on the active side.

In an embodiment, a method is provided that includes receiving imaging data of nervous tissue having a tissue surface. The tissue surface includes at least one of a gap or a projection. The method includes fabricating a mold having a cavity defined by an interior surface. At least a portion of the interior surface has a similar shape as the tissue surface. The mold has a port that provides access to the cavity. The method also includes positioning an array of electrodes within the cavity along the interior surface. The electrodes are electrically coupled to one or more wire conductors that extend to the port of the mold. The method also includes inserting a polymer material into the cavity. The polymer material surrounds the electrodes. The method also includes curing the polymer material to form a lead body having an active side. The active side includes exposed surfaces of the electrodes and has morphological features that are shaped to mate with the surface of the nervous tissue.

In an embodiment, a method is provided that includes acquiring imaging data of nervous tissue of a patient. The nervous tissue has a non-uniform contour. The method also includes communicating the imaging data for fabricating an NS lead having an active side that complements the non-uniform contour of the nervous tissue. The method also includes receiving the NS lead and positioning the NS lead at a target site within the patient such that the active side mates with the non-uniform contour of the nervous tissue.

While multiple embodiments are described, still other embodiments of the described subject matter will become apparent to those skilled in the art from the following detailed description and drawings, which show and describe illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

BRIEF DESCRIPTION OF THE DRAWINGS

FIG. 3A illustrates a cross-section of the NS lead of FIG. 2 taken along the line A-A in FIG. 2.

FIG. 3B illustrates a cross-section of the NS lead of FIG. 2 taken along the line B-B in FIG. 2.

FIG. 11 is a plan view of a NS lead in accordance with an embodiment having windows therethrough.

FIG. 12 is a perspective view of a cross-section of a portion of the NS lead of FIG. 11.

FIG. 13 illustrates a cross-section of the NS lead of FIG. 11 having a subdural position for delivering NS therapy.

DETAILED DESCRIPTION

Figure 1:
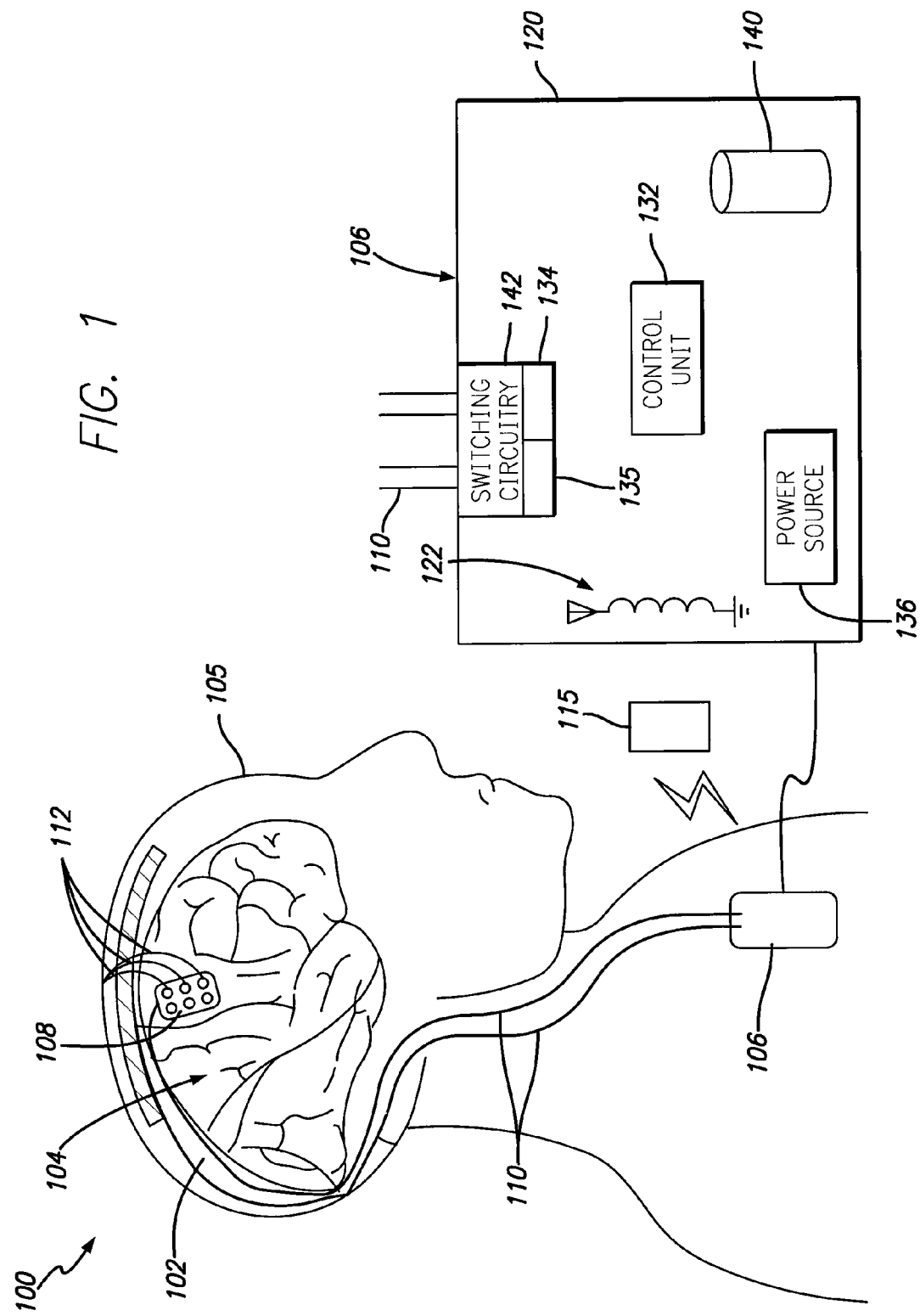
FIG. 1 illustrates a neurostimulation (NS) system in accordance with one embodiment with respect to a patient.

Embodiments described herein include neurostimulation (NS) leads, NS systems, and methods of manufacturing or using the same. A NS system may include a NS lead and a pulse generator that is electrically coupled to the NS lead. The NS lead is configured to be inserted into a space or cavity of a patient and positioned proximate to nervous tissue at a target site. The NS lead may directly engage the nervous tissue (e.g., cortex or a peripheral nerve) or the NS lead may have one or more intervening tissue layers therebetween, such as the dura mater, pia mater, and/or arachnoid mater.

Embodiments set forth herein may be configured or adapted to reduce a likelihood of the NS lead inadvertently moving or migrating from the target site. The NS lead may be shaped and/or utilize different materials to resist movement from the target site. For example, in some embodiments, the NS lead may include an active side having a non-planar contour that is similar to a contour of the nervous tissue at the target site. Projections of the NS lead may be received by depressions in the nervous tissue, and projections of the nervous tissue may be received in depressions of the NS lead. In such embodiments, the non-planar contour of the NS lead may resist lateral movement along the nervous tissue. As used herein, the term "lateral movement" includes any direction along a plane.

It is noted, however, that the non-planar contour of the active side is not required to identically match the contour of the nervous tissue. For example, the contour of the active side may be similar to the contour of the nervous tissue if the active side protrudes at least partially into a void (e.g., sulcus) of the nervous tissue. Alternatively or in addition to resisting inadvertent movement of the NS lead, the non-planar contour of the active side may enable the electrodes to have more intimate positions with respect to the nervous tissue compared to NS leads having flatter sides.

In some embodiments, the NS lead may be compressible or have compressible portions that conform to the contour of the nervous tissue or other anatomical features near the target site. For example, the lead body may have a compressible portion that includes the active side. As the active side is pressed against the target site, the compressible portion may be compressed and/or displaced to conform to a shape of the nervous tissue. In such embodiments, the positions of the electrodes along the active side may be configured to account for movement of the electrodes when the compressible portion is compressed.

In some embodiments, the NS lead has a lead body including windows therethrough. A tissue adhesive may be deposited into the windows and permitted to flow to a surface of the nervous tissue. When the tissue adhesive sets, the tissue adhesive may secure the lead body to the nervous tissue. For example, after the NS lead is positioned at the target site, cyanoacrylate may be deposited into the window(s). The cyanoacrylate may permeate through the window and effectively engage an anatomical surface (e.g., cortical surface or surface of the dura mater) and the lead body. After the cyanoacrylate sets, the cyanoacrylate may impede movement of the NS lead relative to the target site. Tissue adhesives other than cyanoacrylate may also be used.

Although embodiments may be described in terms of cortical stimulation, other embodiments may apply electrical energy to other nervous tissue. For example, in some embodiments, the NS lead may be placed extradurally or within the dura of spinal tissue that can include the ascending and descending tracts of the spinal cord. The spinal tissue can include nervous tissue associated with any of the cervical vertebral segments (C1, C2, C3, C4, C5, C6, C7, C8) and/or any nervous tissue associated with any of the thoracic vertebral segments (T1, T2, T3, T4, T5, T6, T7, T8, T9, T10, T11, T12) and/or any nervous tissue associated with any of the lumbar vertebral segments (L1, L2, L3, L4. L5, L6) and/or any nervous tissue associated with the sacral vertebral segments (S1, S2, S3, S4, S5). In other embodiments, the NS lead may be positioned proximate to various peripheral nervous tissue (e.g., olfactory nerve, optic nerve, oculomotor nerve, trochlear nerve, trigeminal nerve, abducens nerve, facial nerve, vestibulocochlear (auditory) nerve, glossopharyngeal nerve, vagal nerve, accessory nerve, hypoglossal nerve, suboccipital nerve, the greater occipital nerve, the lesser occipital nerve, the greater auricular nerve, the lesser auricular nerve, the phrenic nerve, brachial plexus, radial axillary nerves, musculocutaneous nerves, radial nerves, ulnar nerves, median nerves, intercostal nerves, lumbosacral plexus, sciatic nerves, common peroneal nerve, tibial nerves, sural nerves, femoral nerves, gluteal nerves, thoracic spinal nerves, obturator nerves, digital nerves, pudendal nerves, plantar nerves, saphenous nerves, ilioinguinal nerves, gentofemoral nerves, and iliohypogastric nerves, etc.). Accordingly, it is understood that embodiments set forth herein may have various applications other than cortical stimulation.

FIG. 1 depicts a neurostimulation (NS) system 100 that generates electrical pulses for application to nervous tissue. In the illustrated embodiment, the nervous tissue is a brain 102. In particular embodiments, the NS system 100 is configured to provide electrical pulses to a cortical surface 104 of the brain 102. It should be noted that the particular arrangement of components (e.g., the number, types, placement, or the like) of the illustrated embodiment in FIG. 1 and other illustrated embodiments may be modified in various alternate embodiments. In various embodiments, different numbers of a given element may be employed, a different type or types of a given element may be employed, a given element may be added, and/or a given element may be omitted.

The NS system 100 includes a pulse generator 106 that is configured to generate electrical pulses in order to apply electrical fields to the nervous tissue. The pulse generator 106 is typically implantable within an individual or patient 105 and, as such, may be referred to as an implantable pulse generator (IPG). For example, the pulse generator 106 may be implanted in a thoracic, abdominal, or subclavicular location of the patient 105. In other embodiments, the pulse generator 106 can be implanted in the cranium or just under a scalp of the patient 105.

As shown, the NS system 100 may also include an NS lead 108 that is electrically coupled to the pulse generator 106 through one or more lead cables 110. The pulse generator 106 is configured to control operation of the NS lead 108. In some embodiments, the NS system 100 includes a monitoring system 115 that is configured to communicate with the pulse generator 106. The NS lead 108 is positioned at a target site at or near the cortical surface 104 to generate electrical fields for NS therapy.

In certain embodiments, the NS lead 108 includes an array of electrodes 112 that are configured to generate the electrical fields proximate to the nervous tissue. Each of the electrodes 112 may be selectively controlled to have one or more designated states during operation of the NS lead 108. For example, one or more of the electrodes 112 may function as a source (e.g., anode), one or more of the electrodes 112 may function as a sink (e.g., cathode), and one or more of the electrodes 112 may be inoperative due to, for example, a high impedance. In some embodiments, each of the electrodes 112 is selectively controlled such that each electrode is capable of functioning as a source, sink, or inoperative element over the lifetime of the NS lead 108. The states of the electrodes 112 may be selectively controlled by the pulse generator 106 so that the electrodes 112 may collectively generate designated electrical fields for applying the NS therapy.

In particular embodiments, the array of electrodes 112 is, at least, a two-dimensional array that provides an electrode coverage that is comparable to known paddle leads used in spinal cord stimulation. For instance, the multi-electrode array may be configured to have a coverage similar to Penta™ paddle leads distributed by St. Jude Medical. The array of electrodes 112 may also be a three-dimensional array in which the electrodes have different elevations with respect to one another. Consequently, the electrodes may have different depths with respect to the nervous tissue. The arrays may have a regular pattern. For example, each of the electrodes may have a predetermined spacing with respect to adjacent electrodes. In other embodiments, however, the electrodes may be positioned in an irregular manner such that the spacings between adjacent electrodes are not the same.

FIG. 1 also illustrates a block diagram of the pulse generator 106 in accordance with an embodiment. As shown, the pulse generator 106 includes a housing 120 that is configured to be implanted within the patient 105. The housing 120 may hold a plurality of elements for operating the pulse generator 106, such as a control unit 132, current/voltage sources 134, 135, a power source 136, an inductive coil (or antenna) 122, memory 140, and switching circuitry 142, which may also be characterized as a switch array, switch matrix, or multiplexer. The various elements may be operably coupled to one another for operating the pulse generator 106. One or more elements may be part of or include another element. For instance, the switching circuitry 142 may include the current/voltage sources 134, 135 and/or the switching circuitry 142 and the current/voltage sources 134, 135 may be part of the same hardware unit. Although not shown, the pulse generator 106 may include additional elements or circuitry for operating in the NS system 100 in designated manner (e.g., regulators, capacitors, resistors, transistors, and the like).

As shown, the control unit 132, the current/voltage sources 134, 135, and the switching circuitry 142 are illustrated as separate blocks. It is understood, however, that such distinctions are not necessarily indicative of the division between hardware circuitry. Thus, for example, one or more of the functional blocks (e.g., control unit, the current/voltage sources, switching circuitry, memory) may be implemented in a single piece of hardware or through multiple pieces of hardware. The pulse generator 106 and its elements may control the various modes for providing NS therapy and, optionally, monitoring such NS therapy. More specifically, it is to be understood that the different functions or operations described herein that are performed by the pulse generator 106 and its elements (e.g., the control unit 132, the current/voltage sources 134, 135, the power source 136, the inductive coil 122, the memory 140, and the switching circuitry 142) may be implemented using hardware with associated instructions (e.g., software stored on a tangible and non-transitory computer readable storage medium, such as a computer hard drive, ROM, RAM, or the like) that perform the functions/operations described herein. The hardware may include state machine circuitry hard wired to perform the functions/operations described herein. Optionally, the hardware may include electronic circuits that include and/or are connected to one or more logic-based devices, such as microprocessors, processors, controllers, or the like. Optionally, the components may include processing circuitry such as one or more field programmable gate array (FPGA), application specific integrated circuit (ASIC), or microprocessor. The components in various embodiments may be configured to execute one or more algorithms to perform functions described herein. The one or more algorithms may include aspects of embodiments disclosed herein, whether or not expressly identified in a flowchart or a method.

The inductive coil 122 may be operatively coupled to the control unit 132, the current/voltage sources 134, 135, the power source 136, the memory 140, and the switching circuitry 142. The inductive coil 122 may operate as an antenna that receives communications and/or electrical power. In some embodiments, the inductive coil 122 is configured to receive signals (e.g., instructions or other data) from the monitoring system 115 (FIG. 1) and communicate the signals to the control unit 132, the memory 140, or other elements. The signals may include, for example, software updates, updated stimulation sequences, data regarding conditions of the NS lead 108 or the patient 105, and the like. The inductive coil 122 may also be configured to receive electrical power from the monitoring system 115 and transfer the electrical power to the power source 136.

In some embodiments, the power source 136 may be a rechargeable power source, such as a lithium ion rechargeable (LIR) battery. By way of example only, the capacity of the power source may be from about 20 mAh to about 180 mAh with a nominal voltage of about 3.60V. Examples of suitable LIR batteries includes Eagle Picher LIR 2025, 2430, 2450 and the like or Quallion QL0003I. In some embodiments, the power source 136 may be capable of operating between one week to one month (or more) between charges with about a 100-150 µA stimulation current drain. In addition to supplying the power for transmitting electrical pulses during neurostimulation, the power source 136 may be used to control other functions of the pulse generator 106.

The current/voltage sources 134, 135 may be operably coupled to the electrodes 112 through the switching circuitry 142. Each of the current/voltage sources 134, 135 may be single- or multi-channel and may be capable of delivering a single stimulation pulse or multiple stimulation pulses. In some embodiments, the current/voltage sources 134, 135 and the switching circuitry 142 can be configured to deliver stimulation pulses to multiple channels on a time-interleaved basis, in which case the switching circuitry 142 can time division multiplex the output of current/voltage sources 134, 135 across different electrode combinations at different times to deliver multiple programs or channels of stimulation energy to the patient.

The control unit 132 can control the current/voltage sources 134, 135 and the switching circuitry 142 to generate electrical fields in accordance with parameters specified by one or more neurostimulation parameter sequences (or protocols) stored within the memory 140. Exemplary parameters for the electrical pulses may include a pulse amplitude, pulse width, and pulse rate for a stimulation waveform. Additionally, the control unit 132 can control the switching circuitry 142 to select different electrode configurations for generating the designated electrical fields. Each electrode 112 can be connected as an anode, a cathode, or an inoperative electrode (in which case the electrode is not used for transmitting energy, i.e., is inactive).

For implementation of the elements within NS systems set forth herein, the control unit, current/voltage sources, memory, and switching circuitry may be similar to or function in a similar manner as the elements described in U.S. Patent Application Publication No. 2006/0259098, entitled "SYSTEMS AND METHODS FOR USE IN PULSE GENERATION," which is incorporated herein by reference in its entirety. Circuitry for recharging the power source of the pulse generator using inductive coupling and external charging circuits are described in U.S. Pat. No. 7,212,110, entitled "IMPLANTABLE DEVICE AND SYSTEM FOR WIRELESS COMMUNICATION," which is incorporated herein by reference in its entirety. One or more NS leads may include similar features as the paddle leads described in U.S. Patent Application Publication No. US 2013/0006341, which is incorporated herein by reference in its entirety.

In addition to the above, an example and discussion of "constant current" pulse generating circuitry is provided in U.S. Patent Application Publication No. 2006/0170486 entitled "PULSE GENERATOR HAVING AN EFFICIENT FRACTIONAL VOLTAGE CONVERTER AND METHOD OF USE," which is incorporated herein by reference in its entirety. One or multiple sets of such circuitry may be provided within the NS system 100. Different pulses on different electrodes may be generated using a single set of pulse generating circuitry using consecutively generated pulses according to a "multi-stimset program." Complex pulse parameters may be employed such as those described in U.S. Pat. No. 7,228,179, entitled "METHOD AND APPARATUS FOR PROVIDING COMPLEX TISSUE STIMULATION PATTERNS," and International Patent Publication No. WO 2001/093953 A1, entitled "NEUROMODULATION THERAPY SYSTEM," each of which is incorporated herein by reference in its entirety. Although constant current pulse generating circuitry is contemplated for some embodiments, any other suitable type of pulse generating circuitry may be employed such as constant voltage pulse generating circuitry.

The control unit 132 may control operation of the NS device pursuant to designated stimulation protocols. Each stimulation protocol may include one or more sets of stimulation parameters including pulse amplitude, pulse width, pulse frequency or inter-pulse period, pulse repetition parameter (e.g., number of times for a given pulse to be repeated for respective stimset during execution of program), etc. NS systems, stimsets, and multi-stimset programs are discussed in PCT Publication No. WO 01/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference in their entirety.

When the pulse generator 106 is implanted within the patient 105, the pulse generator 106 may interact with the monitoring system 115. For example, the monitoring system 115 and the pulse generator 106 may communicate with each other one or more times after the pulse generator 106 has been implanted. At later intervals (e.g., once a week, twice a month, once every two months, and the like), the monitoring system 115 and the pulse generator 106 may interact with each other to (i) communicate data between the pulse generator 106 and the monitoring system 115 and/or (ii) charge the power source 136. The communicating and/or charging may be conducted using the inductive coil 122.

Figure 2:
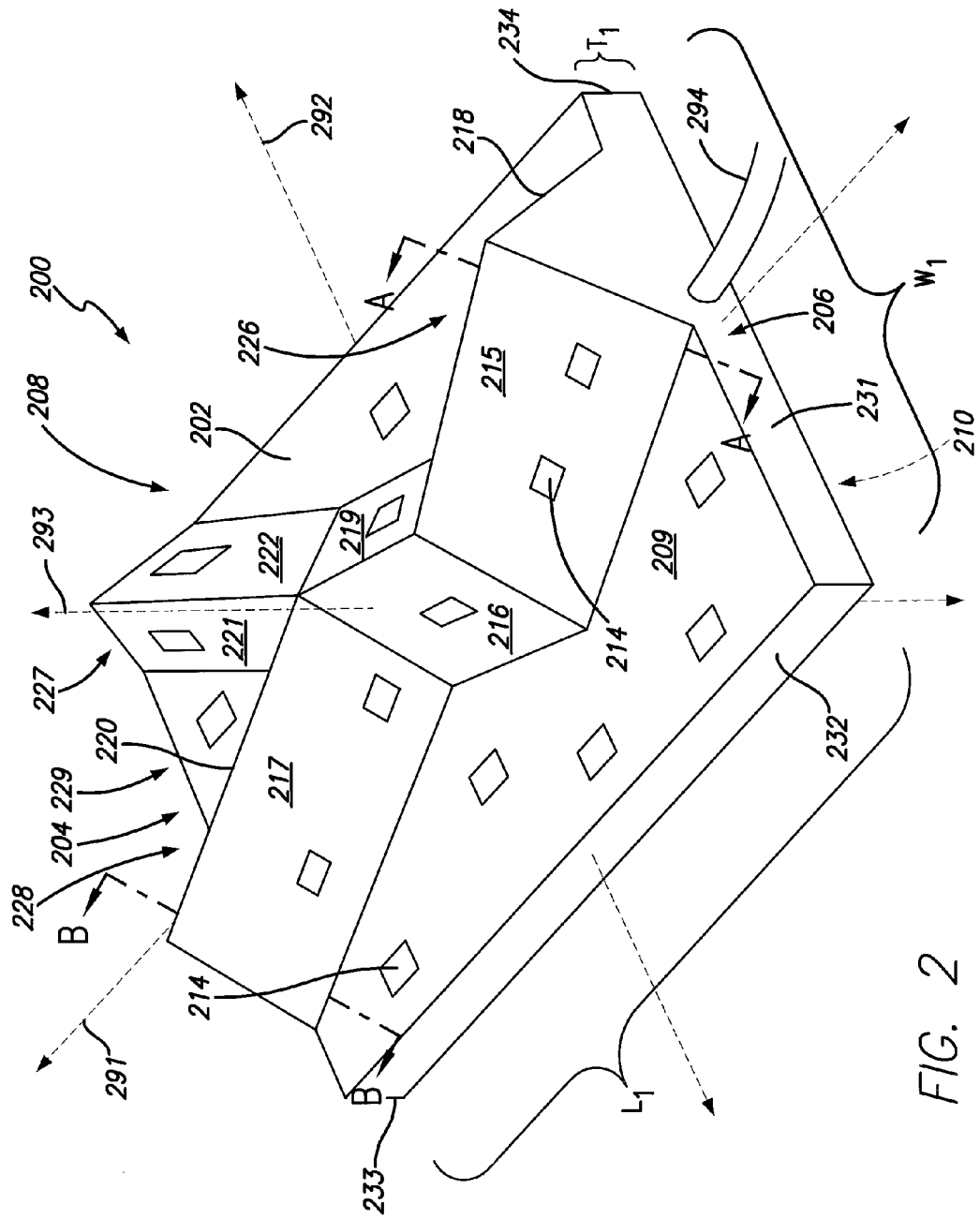
FIG. 2 is a perspective view of a NS lead in accordance with one embodiment that may be used with the NS system of FIG. 1.

FIG. 2 is a perspective view of a NS lead 200 formed in accordance with an embodiment. The NS lead 200 may be used as the NS lead 108 of the NS system 100 (FIG. 1). In particular embodiments, the NS lead 200 has a lead body 202 that is custom-designed to mate or nest with nervous tissue of a particular patient. In such cases, the NS lead 200 may have a compact relationship with respect to the nervous tissue in which the electrodes have more intimate positions with respect to desired stimulation sites and/or the NS lead has a reduced likelihood of inadvertent movement during the lifetime of the NS lead.

For example, as described herein, the NS lead 200 may be manufactured after receiving imaging data of a contour of the nervous tissue. In other embodiments, the lead body 202 may be preformed to have certain features that match common morphologies of the nervous tissue. For instance, a doctor may be permitted to select the most suitable lead configuration out of several possible configurations in a product line. As shown in FIG. 2, the lead body 202 has sharp edges that join adjacent surfaces. In other embodiments, surfaces of the lead body 202 may transition more gently such that sharp edges are not formed.

In the illustrated embodiment, the lead body 202 extends between a first end 204 and a second end 206. The second end 206 is coupled to a lead cable 294, which may be similar to the lead cable 110 (FIG. 1) and include wire conductors (not shown). The lead body 202 has a length $L_1$, a width $W_1$, and a thickness $T_1$. Also shown, the lead body 202 is oriented with respect to mutually perpendicular axes 291-293, which include a longitudinal axis 291 that extends along the length $L_1$, a lateral axis 292 that extends along the width $W_1$, and an elevation axis 293 that extends along the thickness $T_1$. The axes 291-293 may intersect each other at a center of the lead body 202. The longitudinal and lateral axes 291, 292 may define a body plane $P_B$. Although the length $L_1$ is greater than the width $W_1$ in FIG. 2, the NS lead 200 may have alternative configurations in which the length $L_1$ and width $W_1$ are equal or the width $W_1$ is greater than the length $L_1$. Likewise, in other embodiments, the lateral axis 292 may extend along the longer dimension, and the longitudinal axis 291 may extend along the shorter dimension. Also, in the illustrated embodiment, the thickness $T_1$ varies and the length $L_1$ and the width $W_1$ are substantially uniform across the lead body 202. In alternative embodiments, however, the length $L_1$ and the width $W_1$ may not be uniform. For example, the lead body 202 may have a circular or semi-circular profile.

In FIG. 2, the NS lead 200 (or the lead body 202) is in an unflexed or unbiased condition. In some embodiments, the unflexed condition may exist prior to being located at a target site within a patient. In the unflexed condition, the posterior side 210 extends substantially parallel to the body plane $P_B$. In some embodiments, the thickness $T_1$ may be measured along the elevation axis 293 when the NS lead 200 is in the unflexed condition. When the NS lead 200 is operably located at the target site (e.g., after surgery), the NS lead 200 may have a flexed or biased condition. The NS lead 200 may be bent by another anatomical body, such as a bone. As one specific example, the posterior side 210 may be engaged by the cranium such that the lead body 202 is compressed between the cranium and the brain. In some embodiments, the compression may cause the NS lead 200 to bend or curve about the brain. The posterior side 210 may have a contour that is similar to a contour of the cranium. In some cases, the posterior side 210 may have a substantially uniform radius of curvature. In such embodiments, the thickness $T_1$ may be measured along a respective line that extends toward the center of the radius.

The lead body 202 comprises a biocompatible material that is suitable for engaging or interacting with target sites within a patient. Non-limiting examples of such biocompatible materials may include silicone (e.g., silicone rubber), polyvinylchloride (PVC), polyethersulfone, polytetrafluoroethylene (PTFE), polyethylene (e.g., polyethylene terephthalate (PET) film, also known as polyester or Mylar), polyurethane, polyetherimide, polycarbonate, polysulfone, polyetheretherketone (PEEK), polypropylene, polyimide, and the like. In some embodiments, the lead body 202 includes internal elements (e.g., wires, structural supports, etc.) that may or may not be biocompatible. The NS lead 200 has an active side 208 and a posterior side 210 that face in generally opposite directions. The NS lead 200 also includes four body edges 231-234 that extend between the active and posterior sides 208, 210. In the illustrated embodiment, the body edges 231-234 are substantially planar. In alternative embodiments, however, the body edges 231-234 may be non-planar.

The active side 208 is configured to face nervous tissue (e.g., cortex, peripheral nerve, spinal cord, etc.). The active side 208 may directly engage the nervous tissue or may directly engage an intervening anatomical body (e.g., dura mater) that is proximate to the nervous tissue. More than one anatomical body may be intervening between the active side 208 and the nervous tissue. The active side 208 includes an array of electrodes 214 that is configured to provide NS therapy to the nervous tissue. The array is a three-dimensional array in which multiple electrodes 214 extend along each of the longitudinal and lateral axes 291, 292 and at least some of the electrodes 214 have different elevations with respect to others. The electrodes 214 that have different elevations with respect to each other may have different depths with respect to each other and/or the nervous tissue when the NS lead 200 is located at the target site.

The posterior side 210 is configured to face away from the nervous tissue and interface with another anatomical body (e.g., bone, dura mater, other tissue, etc.). The posterior side 210 may have a posterior surface 211 that is substantially planar. In other embodiments, the posterior surface 211 may be shaped to complement an interior surface of the anatomical body that the posterior surface 211 interfaces with in order to urge or predispose the NS lead 200 to a designated position within the patient. The posterior side 210 may or may not include an electrode.

The body edges 231-234 may define a perimeter of the active side 208. In the illustrated embodiment, the perimeter is substantially rectangular when the active side 208 is viewed along the elevation axis 293. In other embodiments, the perimeter may form another shape (e.g., circle, square, or other polygon) when viewed along the elevation axis 293. In particular embodiments, the shape may not have any concave features. In other embodiments, the perimeter may include one or more concave features. For example, the lead body 202 may be S-shaped.

The active side 208 includes an active surface 209, which may be defined by material of the lead body 202 and the electrodes 214. In the illustrated embodiment, the active surface 209 of the active side 208 is substantially continuous within a profile of the lead body 202 defined by the body edges 231-234. In the illustrated embodiment, the lead body 202 does not include windows, holes, or gaps that extend entirely through the lead body 202. Instead, the active surface 209 is continuous such that each point along the active surface 209 within the perimeter smoothly transitions to an adjacent point along the active surface 209 without an immediate drop in elevation due to, for example, a window. As used herein, the term "substantially continuous" may include a limited number of such windows along the active side 208 but with the active surface 209 defining a majority of the active side 208. For example, the active surface 209 may be substantially continuous if the active surface 209 defines more than 80% of the active side 209 having a perimeter defined by the body edges 231-234. In more particular embodiments, the active surface 209 may be substantially continuous if the active surface 209 defines more than 85% of the active side 208 or, more specifically, more than 90% of the active side 208. In some embodiments, the active surface 209 may be entirely continuous along the active side 208 such that the active side 208 is defined only by the material of the lead body 202 and the electrodes 214 and does not include windows. Yet in other embodiments, the NS lead 200 may have an active surface that defines less than or equal to 80% of the active side 208. Such embodiments may include large windows through the lead body or concave features defined by a body edge.

Embodiments set forth herein may include NS leads that have active sides with non-planar contours that are configured to complement a contour of the nervous tissue. The non-planar contours may include one or more morphological features that complement anatomical surfaces of the nervous tissue within the patient. In particular embodiments, the non-planar contours may complement a convoluted or irregular surface of a cortex, which may also be referred to as a cortical surface. A morphological feature may be a localized portion of the active side that projects from or recesses from another portion of the active side that at least partially surrounds or extends along the localized portion. The morphological features may include depressions, such as ravines, notches, valleys, basins, crevices, and the like. These terms are not necessarily mutually exclusive. For example, a ravine may also constitute a valley or crevice. The morphological features may also include projections, such as ridges, hills, peaks, plateaus, and the like. Again, these terms are not necessarily mutually exclusive. The depressions or projections may extend along respective paths in directions that are generally parallel to the body plane. In many cases, the designated path is not linear.

Because a morphological feature may be defined by changes in elevation as the morphological feature extends along the active surface in at least one of a longitudinal direction or a lateral direction, a morphological feature may have a 3D shape that is defined, at least in part, by other morphological features. For example, a valley may be defined between two or more projections or a basin may be defined by a single ridge that encircles the basin. The 3D shape of a projection may be defined by a plurality of slopes that extend toward a common elevated peak or line. Whereas the slopes that define a projection generally face in directions away from each other, the slopes that define a depression may face each other.

In many cases, the 3D shape of the morphological feature may be non-uniform such that the 3D shape of the morphological feature changes as the morphological feature extends across the active side. For example, a path taken by the morphological feature across the active side may be non-linear and/or a cross-sectional shape of the morphological feature (e.g., taken transverse to a direction of the path) may change as the morphological feature extends along the active side.

In some embodiments, the non-planar contour may correlate to a change in the thickness $T_1$ of the lead body 202. For example, as the lead body 202 extends along the lateral axis 292 or the longitudinal axis 291, the thickness $T_1$ defined between a posterior surface 211 of the posterior side 210 and the active surface 209 changes. In particular, projections may correspond to an increased thickness $T_1$ and depressions may correspond to a reduced thickness $T_1$. Alternatively or in addition to changes in the thickness $T_1$, the non-planar contour may correlate to changes in elevation of the active surface 209. The elevation may be measured along the elevation axis 293 relative to the body plane $P_B$ defined by the longitudinal and lateral axes 291, 292. In some embodiments, the elevation may be measured relative to a lowest point along active surface 209.

As shown in FIG. 2, the active surface 209 has a non-planar contour that includes a plurality of slopes 215-222. The slopes 215-222 form morphological features 226-229 that extend across the active side 208. The morphological features 226-228 are ridges or hills and the morphological feature 229 is a valley that is defined between the morphological features 227, 228. Specifically, the morphological feature 226 is defined between the slopes 215, 218 and between the slopes 216, 219. The morphological feature 227 is defined between the slopes 221, 222. The morphological feature 228 is defined between the slopes 217, 220. The morphological feature 229 is defined between the opposing slopes 220, 221. Additional examples of morphological features are described herein.

As shown in FIG. 2, the morphological features 226-229 may include one or more of the electrodes 214. Because the morphological features 226-229 correspond to changes in the thickness $T_1$ and/or changes in an elevation of the active surface 209, the array of the electrodes 214 may be a three-dimensional array in which at least two of the electrodes are positioned to have different depths or elevations with respect to one another and/or the nervous tissue.

As described herein, one or more of the morphological features for some embodiments may be non-uniform such that a contour of the morphological feature changes as the morphological feature extends across the active side. By way of example, a path taken by the morphological feature 226 across the active side 208 may be non-linear. As the morphological feature 226 extends along the longitudinal axis 291, the path taken by the morphological feature 226 changes directions. More specifically, the morphological feature 226 moves toward the body edge 232 for a designated distance and then changes direction to move toward the body edge 234. In some embodiments, the path may be represented by a line that intersects the highest points of each cross-section of the morphological feature.

In the illustrated embodiment, the change in direction by the path of the morphological feature 226 is abrupt. However, in other embodiments, the morphological feature 226 may curve toward the other direction. In some embodiments, the morphological feature 227 or the morphological feature 228 may be considered part of the morphological feature 226. As such, the path of the morphological feature 226 may change directions again as the morphological feature 226 extends along the longitudinal axis 291. In some embodiments, morphological features may intersect each other at a joint and extend therefrom (or thereto) in different directions. For instance, the morphological features 226-228 intersect each other at a joint 249.

FIG. 3A is a cross-section of the NS lead 200 taken along the line A-A in FIG. 2 and illustrates, in particular, a cross-section of the morphological feature 226. FIG. 3B is a cross-section of the NS lead 200 taken along the line B-B in FIG. 2 and illustrates, in particular, a cross-section of the morphological features 228. The cross-sections are taken transverse to a direction of the path of the respective morphological feature.

In FIG. 3A, the morphological feature 226 is defined between the slopes 215 and 218. The slopes 215, 218 extend from respective base surfaces 282, 284, respectively, toward each other and intersect each other at a peak 286. In FIG. 3B, the morphological feature 228 is defined between the slopes 217 and 220. The slopes 217, 220 extend from respective base surfaces 288, 289, respectively, toward each other and intersect each other at a peak 290.

As used herein, the term "slope" includes a surface that is inclined relative to a body plane or a base surface of the lead body. In the illustrated embodiment, the inclined surfaces of the slopes 215, 218 and 217, 220 are linear such that the inclined surfaces form a constant angle with respect to the body plane $P_B$ (or the corresponding base surface). However, in other embodiments, the angles may change along the surface of the corresponding slope. For instance, a slope may gradually decrease as the slope approaches a corresponding peak. For each of the slopes 215, 218, 217, 220, the angle of the corresponding slope is consistently positive or consistently negative throughout the corresponding slope. For example, with respect to the body plane $P_B$, each of the slopes 215, 218 consistently extends away from the body plane $P_B$ to the peak 286 without any portion extending toward the body plane $P_B$ prior to reaching the peak 286.

In some embodiments, a cross-sectional shape of the morphological feature may change as the morphological feature extends along the active side. By way of example, the cross-section of FIG. 3A is proximate to the second end 206, and the cross-section of FIG. 3B is proximate to the first end 204. As shown by comparing FIGS. 3A and 3B and viewing FIG. 2, the cross-sectional shape of the morphological feature 226 changes as the morphological feature 226 extends along the longitudinal axis 291 and transitions into the morphological feature 227 and/or 228. More specifically, a cross-sectional shape of the morphological feature 226 changes as the morphological feature 226 extends along the longitudinal axis 291. The changing of the cross-sectional shape may correspond with a change in the contour of the target site.

Figure 4:
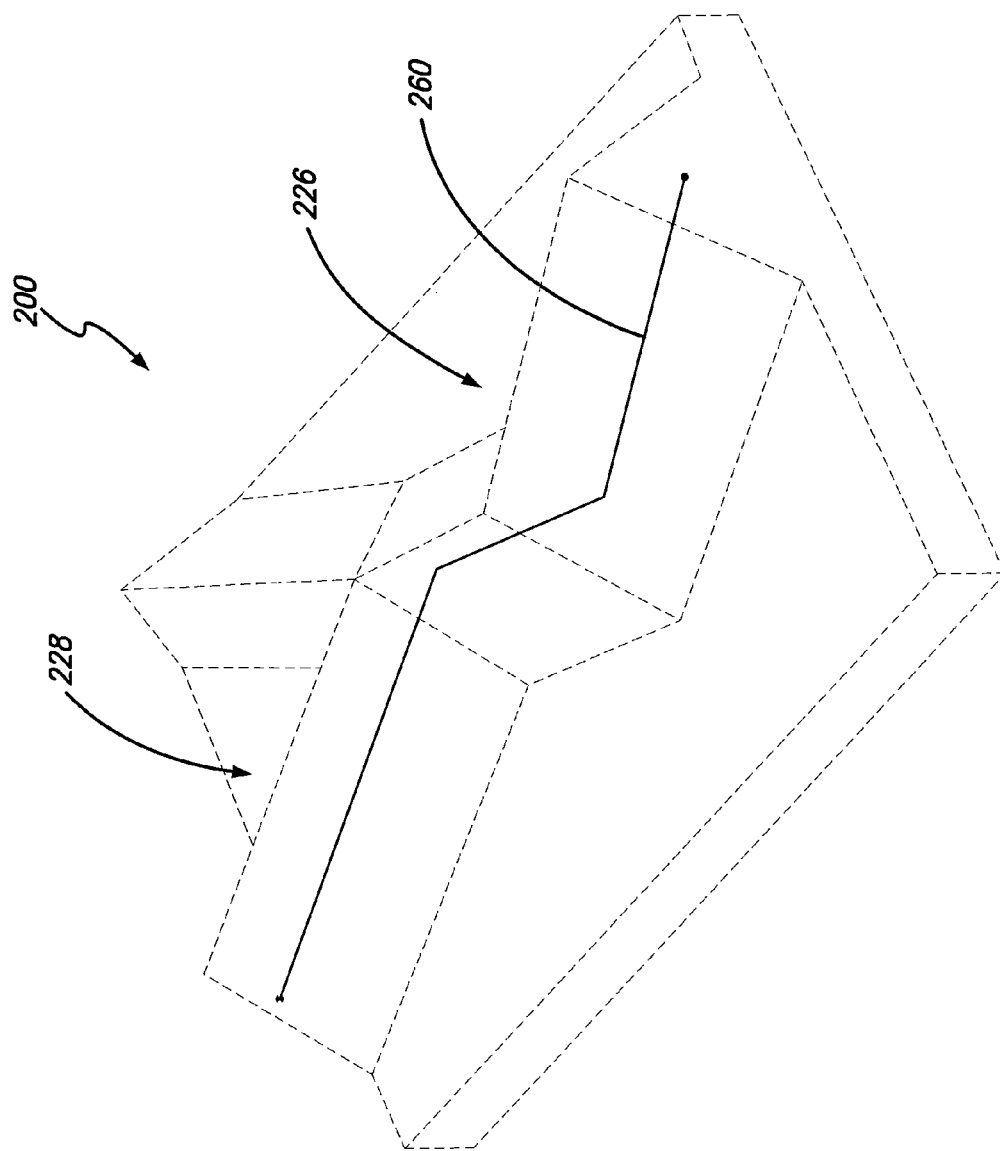
FIG. 4 is the perspective view of the NS lead in FIG. 2 with edges dashed to more clearly indicate a centerline extending through the NS lead.

FIG. 4 illustrates the NS lead 200 in the identical perspective view shown in FIG. 2. In FIG. 4, edges of the lead body 202 have been dashed to more clearly indicate a centerline 260. The centerline 260 extends through the morphological features 226 and 228. As described herein, the morphological features 226 and 228 may be considered as a single morphological feature. In some embodiments, a designated path of a morphological feature may be represented by a centerline that extends through a center of the morphological feature along the designated path. For example, the centerline may be a series of interconnected points in which each point is a geometric center of a cross-section of the morphological feature. As shown in FIG. 4, the centerline 260 extends through a center of the morphological features 226, 228 along the designated path. Different points of the centerline 260 are illustrated in FIGS. 3A and 3B. As shown, each point of the centerline 260 is at a geometric center of the cross-sectional shape.

A centerline (or a designated path) of a morphological feature may have a variety of configurations. The centerline may change directions at one or more points and/or continuously (e.g., during a curve). In some embodiments, the configuration of the centerline may be based on the contour of the nervous tissue. As a specific example, the configuration of the centerline may be based on the configuration of a sulcus or gyrus of a cortex that the corresponding morphological feature interfaces with. One or more portions of a centerline may be linear. The linear portions may extend parallel to either of the longitudinal axis or the lateral axis of the lead body, or the linear portions may extend at an angle with respect to the longitudinal and lateral axes. The linear portions may extend toward the body plane (decrease in elevation), away from the body plane (increase in elevation), or parallel to the body plane (maintain elevation). Similarly, one or more portions of a centerline may be curved. The curved portions may curve away from the body plane (increase in elevation), toward the body plane (decrease in elevation), or parallel to the body plane (maintain elevation). Portions of the centerline may be winding, tortuous, wavy, or serpentine.

Figure 5:
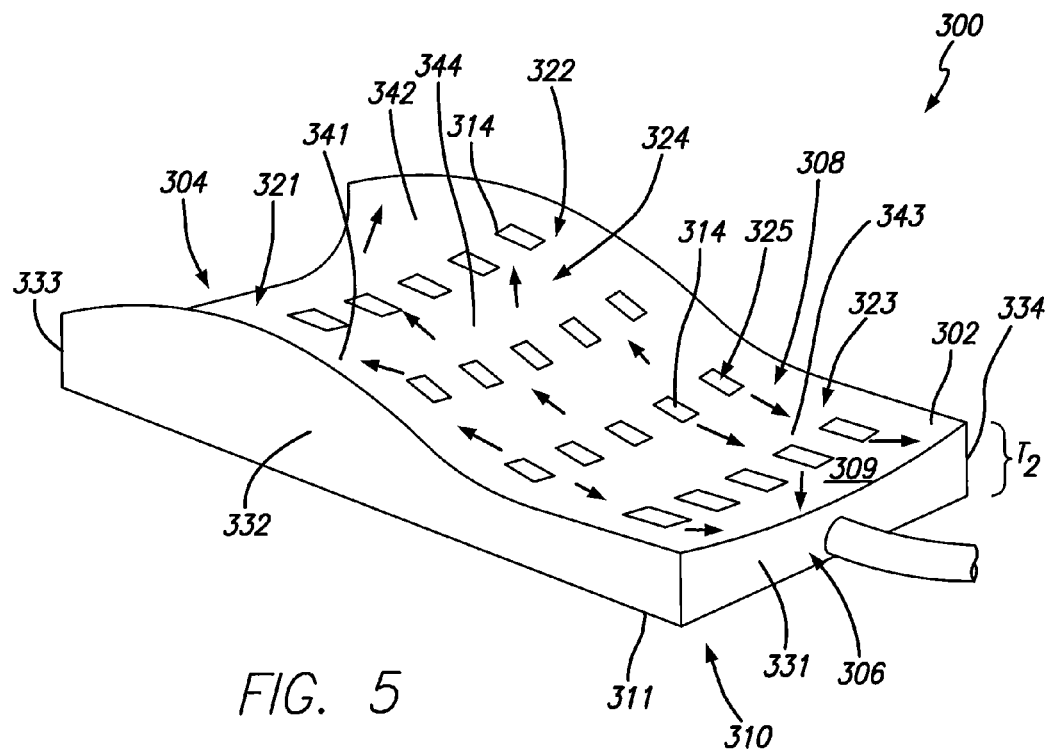
FIG. 5 is a perspective view of a NS lead in accordance with an embodiment that may be used with the NS system of FIG. 1.

FIG. 5 is a perspective view of a NS lead 300 formed in accordance with one embodiment. The NS lead 300 may be used as the NS lead 108 with the NS system 100 (FIG. 1). The NS lead 300 may have similar features or characteristics as the NS lead 200 (FIG. 2) and/or the NS lead 108 (FIG. 1). For instance, the NS lead 300 includes a lead body 302 that extends between a first end 304 and a second end 306. The NS lead 300 also has an active side 308 and a posterior side 310 that face in generally opposite directions. The active side 308 includes an array of electrodes 314 that are configured to provide NS therapy to nervous tissue.

The NS lead 300 also includes four body edges 331-334 that extend between the active and posterior sides 308, 310. The body edges 331-334 may define a perimeter or profile of the active side 308 and the posterior side 310. The active side 308 has an active surface 309, and the posterior side 310 has a posterior surface 311. In the illustrated embodiment, the active surface 309 and the posterior surface 311 are entirely continuous within the respective perimeter. In other embodiments, the active surface 309 and/or the posterior surface 311 may be substantially continuous. Alternatively, the lead body 302 may have numerous windows or gaps therethrough.

The active surface 309 has a non-planar contour including a plurality of slopes 341-344. Similar to the NS lead 200 (FIG. 2), the non-planar contour may correlate to a change in a thickness $T_2$ of the lead body 302 and or a change in elevation of the active surface 309 with respect to a body plane (not shown). To distinguish the different slopes 341-344 in FIG. 5, the active surface 309 has arrows thereon that point in directions of increasing elevation. For example, the slope 341 increases in elevation as the active surface 309 extends toward the body edge 332 proximate to the first end 304. The slope 342 increases in elevation as the active surface 309 extends toward the body edge 334 proximate to the first end 304. The slope 343 increases in elevation as the active surface 309, proximate to the second end 306, extends toward the body edge 331. The slope 344 increases in elevation as the active surface 309 extends from a central area of the active surface 309 toward the first end 304. The slopes 341-344 form morphological features 321-325 that that extend across the active side 308. As used herein, the phrase "across the active side" comprises the morphological feature extending only partially along the active side. The phrase does not require that the morphological feature extend entirely across the active side.

The morphological features 321-323 are projections (e.g., ridges or hills) and the morphological feature 324, 325 are depressions (e.g., valleys or basins). In the illustrated embodiment, the morphological feature 324 is a valley that is defined between the morphological features 321, 322. The morphological feature 325 may be characterized as a basin located between the morphological feature 324, which increases in elevation as the slope 344 extends away from the morphological feature 325, and the morphological feature 323, which also increases in elevation as the slope 343 extends away from the morphological feature 325. As shown, each of the morphological features 321-325 includes one or more of the electrodes 314. Accordingly, the array of the electrodes 314 is a three-dimensional array in which at least some of the electrodes 314 have different elevations with respect to a body plane (not shown). In alternative embodiments, one or more of the morphological features may not have an electrode 314.

Figure 6:
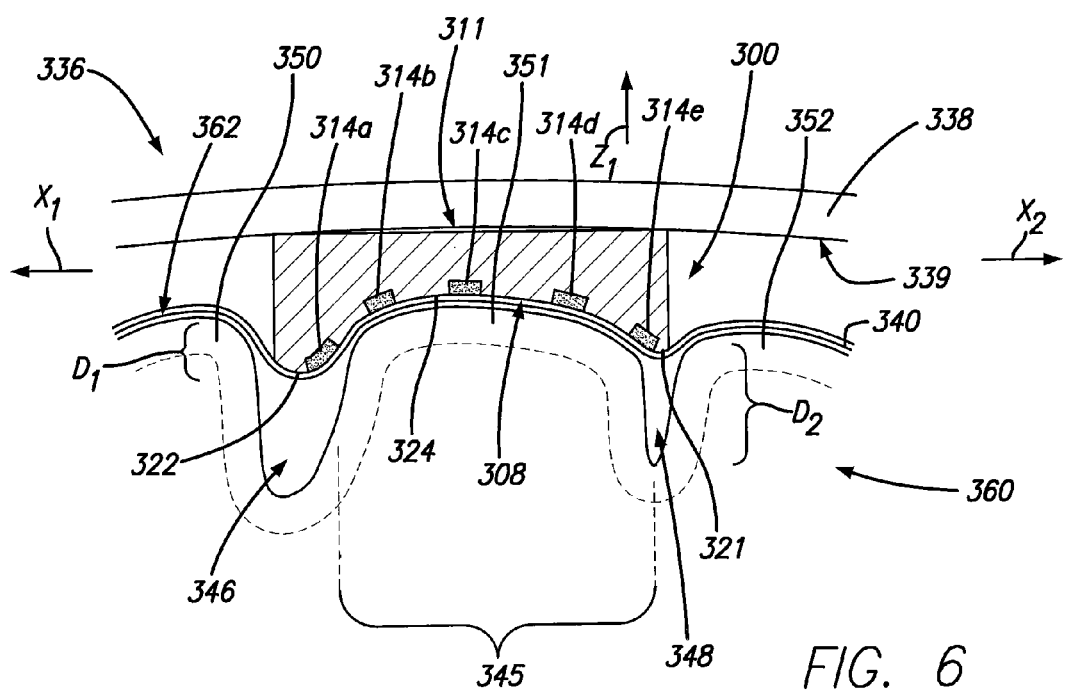
FIG. 6 illustrates a cross-section of the NS lead of FIG. 5 having an epidural position for delivering NS therapy.

FIG. 6 illustrates a cross-section of an NS lead 300 in an operable position within a patient. More specifically, the NS lead 300 is positioned within a head 336 of a patient. The head 336 includes bone 338 of a cranium, a dura mater 340, and a cortex 360 having a cortical surface 362. The cortical surface 362 defines gaps or fissures 346, 348 and plateaus or ridges 350-352. The gaps 346, 348 are hereinafter referred to as sulci 346, 348 and the plateaus are hereinafter referred to as gyri 350-352. The cortical surface 362 includes a target site 345 that constitutes an approximate area of the cortical surface 362 that is intended to receive electrical energy from the NS lead 300. The target site 345 is indicated by a bold line along the cortical surface 362 in FIG. 6.

The NS lead 300 is positioned in an epidural manner such that the NS lead 300 is positioned between the bone 338 and the dura mater 340. The active side 308 of the NS lead 300 directly engages the dura mater 340 and effectively interfaces with the cortical surface 362. As used herein, an active side may "effectively interface with" a surface of the nervous tissue if the active side directly engages the surface or if the active side directly engages an intervening layer or fluid that is proximate to the surface. When the active side effectively interfaces with a surface of the nervous tissue, the electrodes along the active side may be capable of providing NS therapy to the nervous tissue.

In FIG. 6, the electrodes of the NS lead 300 are specifically referenced as electrodes 314A-314E. As shown, the ridge 322 extends into the sulcus 346 by a depth $D_1$, and the ridge 321 extends into the sulcus 348 by a depth $D_2$. The valley 324 extends along the gyrus 351. As shown, the electrodes 314A and 314E may have different depths into the cortex 360 compared to each other and the other electrodes 314B-314D. More specifically, the electrodes 314A and 314E may be positioned at least partially within respective depressions caused by the sulci 346, 348. The electrodes 314B-314D are positioned to effectively interface with the cortical surface 362 along the gyrus 351.

Due to the morphological features 321, 322, 324, the active side 308 may mate or nest with the cortical surface 362 along the target site 345. As such, the nervous tissue and the NS lead 200 may fit compactly with each other. For example, the non-planar contour of the active side 308 may complement the non-planar (or convoluted) contour of the cortical surface 362 such that active side 308 fits or mates with the target site 345. In such configurations, the electrodes 314A-314E may have different operable depths into the cortex 360 or different elevations with respect to each other. In particular embodiments, despite the non-planar contour of the cortical surface 362, each of the electrodes 314A-314E is capable of having an intimate (e.g., closer) position with respect to the cortical surface 362 for delivering the NS therapy.

In addition to an intimate position, the non-planar contour of the active side 308 may reduce the likelihood of migration of the NS lead 300. As shown, the ridges 322, 321 may impede lateral movement of the NS lead 300, which is indicated by the arrows $X_1$, $X_2$. In some embodiments, the ridges 322, 321 may also impede lateral movement into and out of the page of FIG. 6. For example, the ridges 322, 321 may have a varying cross-sectional shape in which portions of the ridges 322, 321 that have larger cross-sectional shapes may resist movement into portions of the corresponding sulci that have gaps that are not large enough to receive the ridges 322, 321.

Also shown, the posterior side 310 may directly engage an interior surface 339 of the bone 338. In some embodiments, the thickness $T_2$ (FIG. 5) and a shape of the posterior side 310 may be configured so that the bone 338 engages the posterior side 310 to facilitate holding the NS lead 300 within a designated position along the target site 345. As such, the NS lead 300 may be shaped so that the NS lead 300 blocks movement in a direction away from the cortical surface 362 (as indicated by arrow $Z_1$). Accordingly, the non-planar contour of the active side 308 may impede movement of the NS lead 300 in any direction along the target site 345 or away from the target site 345.

Figure 7:
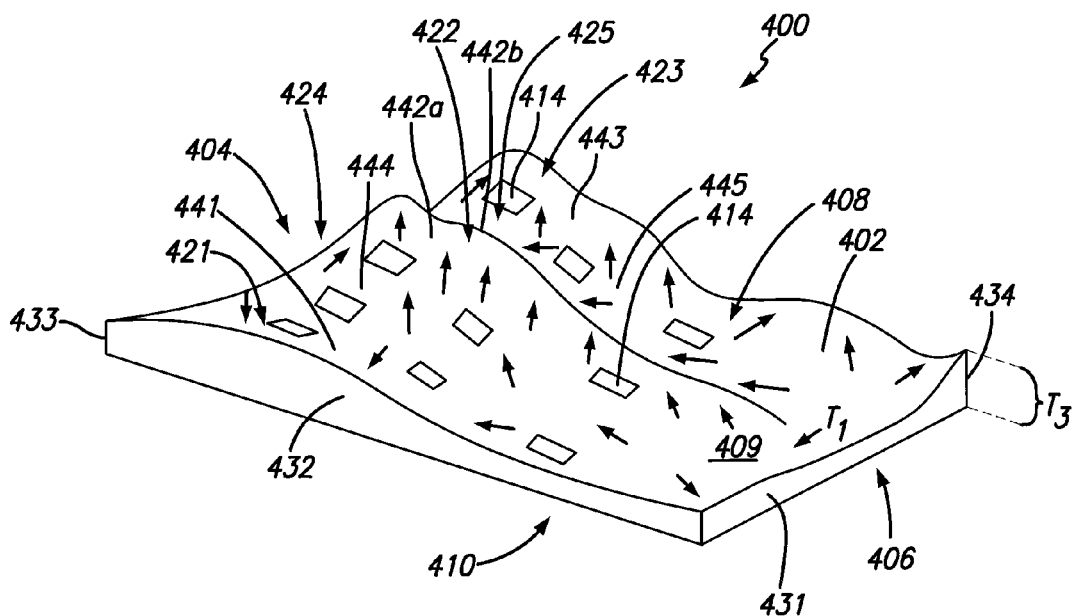
FIG. 7 is a perspective view of a NS lead in accordance with an embodiment that may be used with the NS system of FIG. 1.

FIG. 7 is a perspective view of an NS lead 400 formed in accordance with an embodiment that may be used with the NS system 100 (FIG. 1). The NS lead 400 may have similar features or characteristics as the NS lead 108 (FIG. 1), the NS lead 200 (FIG. 2), or the NS lead 300 (FIG. 5). For instance, the NS lead 400 includes a lead body 402 that extends between a first end 404 and a second end 406. The NS lead 400 also has an active side 408 and a posterior side 410 that face in generally opposite directions. The active side 408 includes an array of electrodes 414 that is configured to provide NS therapy to nervous tissue.

The NS lead 400 also includes four body edges 431-434 that extend between the active and posterior sides 408, 410. The body edges 431-434 may define a perimeter of the active side 408. The active side 408 has an active surface 409. In the illustrated embodiment, the active surface 409 is entirely continuous within the perimeter. In other embodiments, active surface 409 may be substantially continuous. Alternatively, the active surface 409 may have numerous windows or gaps.

The active surface 409 has a non-planar contour including a plurality of different slopes 441-445. To distinguish the different slopes 441-445 in FIG. 7, the active surface 409 has arrows thereon that point in directions of increasing elevation. Similar to the NS leads 200 (FIG. 2) and 300 (FIG. 5), the non-planar contour may correlate to a change in a thickness $T_3$ of the lead body 402 and or a change in elevation of the active surface 409 with respect to a body plane (not shown). The slopes 441-445 form morphological features 421-425 that that extend across the active side 408.

The morphological features 421-423 are projections (e.g., ridges or hills) and the morphological feature 424, 425 are depressions (valleys or basins). In the illustrated embodiment, the morphological feature 422 is defined by the slopes 442A, 442B that extend toward and intersect each other at a top of the morphological feature 422. The morphological feature 424 is a valley that is defined between the morphological features 421, 422. The morphological feature 425 may be characterized as a valley located between the morphological features 422, 423. As shown, each of the morphological features 421-425 includes one or more of the electrodes 414.

Figure 8:
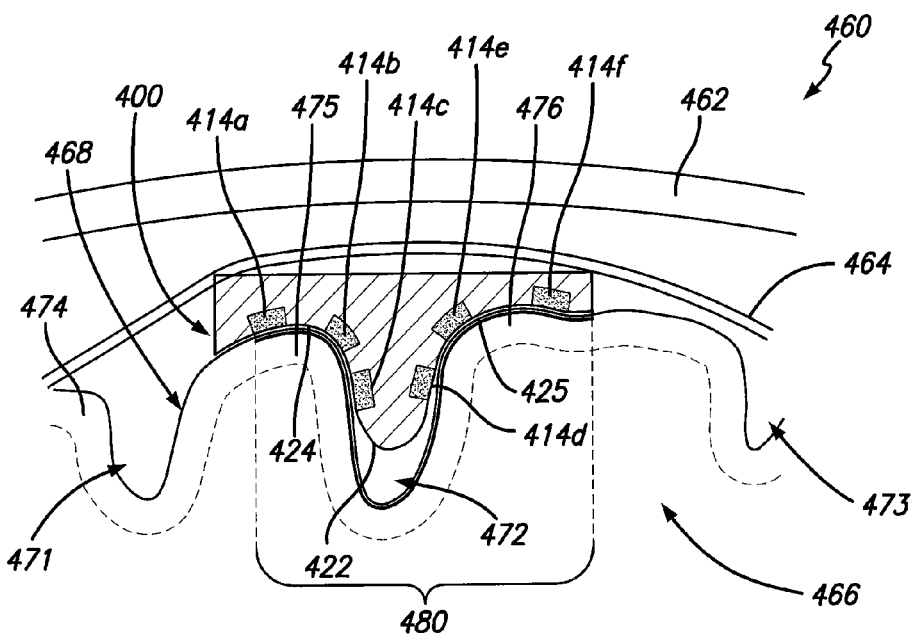
FIG. 8 illustrates a cross-section of the NS lead of FIG. 7 having a subdural position for delivering NS therapy.

FIG. 8 illustrates a cross-section of the NS lead 400 in an operable position within a patient. Similar to the NS lead 300 in FIG. 6, the NS lead 400 is positioned within a head 460 that includes bone 462 of a cranium, a dura mater 464, and a cortex 466 having a cortical surface 468. The cortical surface 468 defines sulci 471-473 and gyri 474-476. The cortical surface 468 includes a target site 480 that is configured to receive electrical energy from the NS lead 400. The target site 480 is indicated by a bold line along the cortical surface 468. The NS lead 400 is positioned in a subdural manner such that the NS lead 400 is positioned between the dura mater 464 and the cortical surface 468. The active side 408 of the NS lead 400 directly engages and effectively interfaces with the cortical surface 468 at the target site 480.

As shown, the target site 480 includes the cortical surface 468 along the gyri 475, 476 and the sulcus 472 between the adjacent gyri 475, 476. The electrodes are specifically referenced as electrodes 414A-414F in FIG. 8 and extend across the cortical surface 468. As shown, the electrodes 414A-414F provide a coverage that spans across the sulcus 472 and includes both of the gyri 475, 476. The ridge 452 extends into the sulcus 472 and the valleys 455, 456 extend along the gyri 475, 476, respectively. The electrodes 414C and 414D are located within the sulcus 472 at a greater depth than the electrodes 414A, 414B 414E, and 414F. The electrodes 414A, 414B directly engage the gyrus 475 and the electrodes 414E, 414F directly engage the gyrus 476.

Due to the morphological features 421-425, the active side 408 may mate with the cortical surface 468 along the target site 480. Again, the non-planar contour of the active side 408 may complement the non-planar (or convoluted) contour of the cortical surface 468 such that active side 408 fits or mates with the cortical surface 468 along the target site 480. Thus, despite the non-planar contour of the cortical surface 468, each of the electrodes 414A-414F is capable of having an intimate position with respect to the cortical surface 468 for delivering the NS therapy. In addition to a more intimate position, the morphological features 421-425 may reduce the likelihood of migration of the NS lead 400 by impeding movement of the NS lead 400 in any direction as described above with respect to the NS lead 300.

Figure 9:
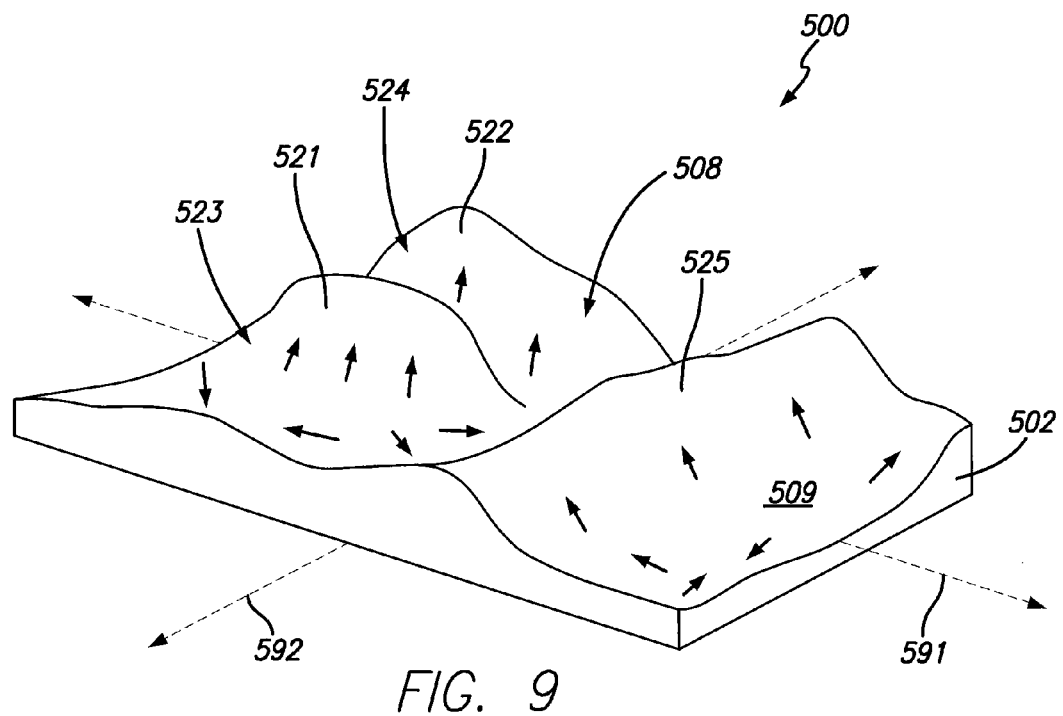
FIG. 9 is a perspective view of a NS lead in accordance with an embodiment that may be used with the NS system of FIG. 1.

FIG. 9 is a perspective view of a NS lead 500 formed in accordance with an embodiment. As shown, the NS lead 500 includes a lead body 502 that is oriented with respect to a longitudinal axis 591 and a lateral axis 592, which are perpendicular to each other. The lead body 502 includes an active side 508 having an active surface 509 including a plurality of slopes (generally indicated by arrows). The slopes form morphological features 521-525. The morphological features 521 and 522 are ridges that extend lengthwise in a first direction that is generally parallel to the longitudinal axis 591. The morphological features 523 and 524 are valleys that also extend lengthwise in the first direction. The morphological feature 525, however, is a ridge that extends lengthwise in a second direction that is generally parallel to the lateral axis 592 and generally transverse to the first direction. Although not shown, the NS lead 500 is configured to include a plurality of electrodes.

Accordingly, the NS lead 500 has multiple morphological features that extend in different directions. The morphological features 521-524 extend substantially transverse to the morphological feature 525. More specifically, in the illustrated embodiment, each of the morphological features 521-524 extends along a path that is substantially perpendicular to a path taken by the morphological feature 525. In such embodiments, the morphological features 521-524 may impede movement of the NS lead 500 in lateral directions that are parallel to the lateral axis 592, and the morphological feature 525 may impede movement of the NS lead 500 in lateral directions that are parallel to the longitudinal axis 591. Collectively, the morphological features 521-525 may impede lateral movement in any direction along the nervous tissue.

In the illustrated embodiment, each of the morphological features 521-525 extends lengthwise in substantially one respective direction. In other embodiments, a morphological feature may extend in more than one direction such that the morphological feature takes a tortuous or winding path. For example, the morphological feature 226 (FIG. 2) extends in different directions. In some embodiments, at least a portion of a path taken by a first morphological feature may extend substantially transverse to at least a portion of a path taken by a second morphological feature. Paths may be substantially transverse if the morphological features extend in different directions that form an angle that is at least 45°. In particular embodiments, the angle may be at least 60° or, more particularly, at least 75°.

Figure 10:
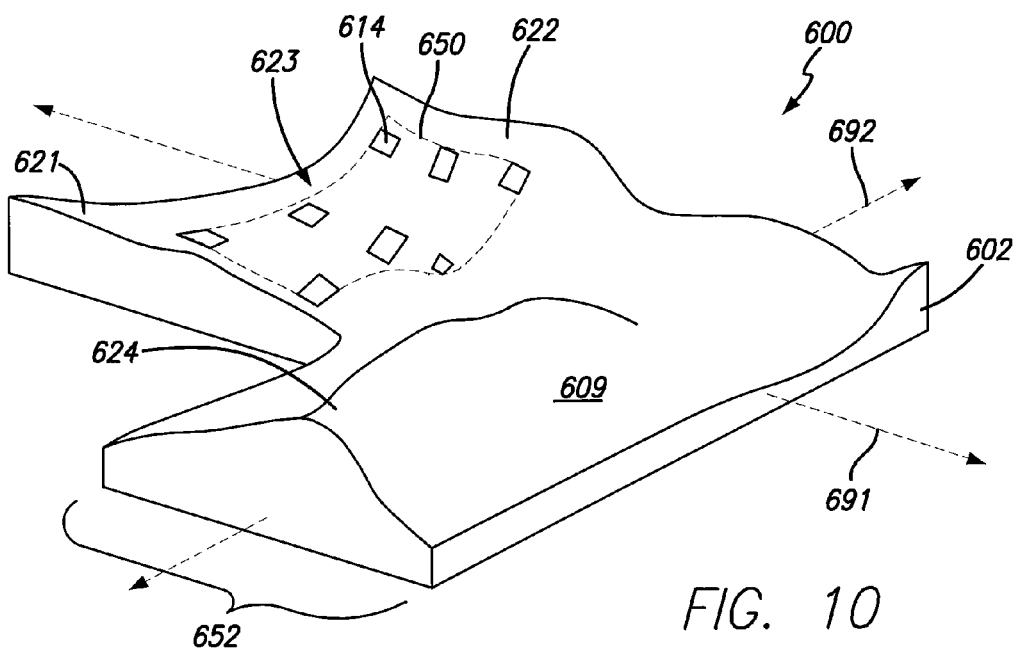
FIG. 10 is a perspective view of a NS lead in accordance with an embodiment that may be used with the NS system of FIG. 1.

FIG. 10 is a perspective view of a NS lead 600 formed in accordance with an embodiment. As shown, the NS lead 600 includes a lead body 602 that is oriented with respect to a longitudinal axis 691 and a lateral axis 692, which are perpendicular to each other. The lead body 602 includes an active side 608 having an active surface 609 including a plurality of slopes (not indicated). The slopes form morphological features 621-624. The morphological features 621 and 622 are ridges that extend lengthwise in a first direction that is generally parallel to the longitudinal axis 691. The morphological feature 623 is a valley between the morphological features 621, 622 that extend lengthwise in the first direction. The morphological feature 624, however, is a ridge that extends lengthwise in a second direction that is generally parallel to the lateral axis 692 and generally transverse to the first direction.

The active side 608 includes an array of electrodes 614. The active surface 609 includes an electrode area 650, which is indicated by the dashed lines along the active surface 609. An electrode area may be an area along an active surface that includes an entirety of an array of electrodes. For example, the electrode area 650 may have a perimeter that circumscribes each of the electrodes 614 of the array. The perimeter may extend along the outer electrodes of the array and, when extending between adjacent electrodes, extend along a shortest possible path. As shown, the electrode area 650 extends along portions of the morphological features 621-623.

In some embodiments, if a target site of the nervous tissue that is intended to be stimulated does not have a varying contour, but another area proximate to the target site has a varying contour, then the NS lead may be manufactured to include an additional portion(s) with morphological features configured to interact with the other area. In other words, the NS lead may be fabricated to not only (a) provide an area for an array of electrodes, but also (b) provide a morphological feature(s) for impeding movement of the NS lead. For example, as shown in FIG. 10, the lead body 602 includes a grip portion 652. The grip portion 652 is an extraneous portion of the lead body 602 that is void of any one of the electrodes 614 and/or does not include a portion of the electrode area 650. However, the grip portion 652 includes at least a portion of the morphological feature 624.

FIG. 11 is a plan view of a NS lead 700 in accordance with one embodiment, and FIG. 12 illustrates a perspective of a cross-section of a portion of the NS lead 700. For reference, the NS lead 700 is oriented with respect to a longitudinal axis 791 and a lateral axis 792 (FIG. 11), which are perpendicular to each other and intersect within the lead body 702. The NS lead 700 may be used with the NS system 100 (FIG. 1) and may have features that are similar to the other NS leads described herein. In the illustrated embodiment, the NS lead 700 includes a lead body 702 having a substantially uniform thickness $T_4$ (FIG. 12). In other embodiments, the lead body 702 may have a varying thickness $T_4$, similar to the NS leads described above.

The lead body 702 includes an active side 708 (FIG. 12) and a posterior side 710 that face in generally opposite directions. The NS lead 700 also includes an array of electrodes 714 that have designated positions within the lead body 702. In the illustrated embodiment, the electrodes 714 are positioned in a regular array in which the spacings between adjacent electrodes 714 are substantially equal along the longitudinal axis 791 and the lateral axis 792. More specifically, the electrodes 714 in rows that extend parallel to a longitudinal axis 791 may have substantially equal spacings $S_1$, and the electrodes 714 in columns that extend parallel to the lateral axis 792 may have substantially equal spacings $S_2$. In other embodiments, however, the pattern may be irregular such that the spacings are not equal. As shown in FIG. 11, the electrodes 714 are electrically coupled to wire conductors 716. The wire conductors 716 extend into the lead body 702 from a lead cable 701. By way of example only, the wire conductors 716 may include MP35N (e.g., Nickel-Cobalt MP35 base alloy) with silver core and coated with ethylene tetrafluoroethylene (ETFE) insulation. A diameter of the wire conductor 716 may be from about 0.0005 inches (0.00127 centimeters) to about 0.002 inches (0.00508 centimeters). Other materials and/or dimensions may be used.

In particular embodiments, the thickness $T_4$ is sufficiently thin to permit the lead body 702 to conform to a non-uniform contour of nervous tissue, such as a cortex. The thickness $T_4$ may be from about 0.0005 inches (0.00127 centimeters) to about 0.003 inches (0.00762 centimeters). To this end, the lead body 702 may include one or more flexible materials that permit the lead body 702 to conform to a non-planar surface. Non-limiting examples of such materials may include silicone, polyvinylchloride (PVC), polyethersulfone, polytetrafluoroethylene (PTFE), polyethylene (e.g., polyethylene terephthalate (PET) film, also known as polyester or Mylar), polyurethane, polyetherimide, polycarbonate, polysulfone, polyetheretherketone (PEEK), polypropylene, polyimide, and the like. In some embodiments, the lead body 702 may also include a mesh material 712 that extends within the lead body 702 along a body plane defined by the longitudinal and lateral axes 791, 792. The mesh material 712 may include a membrane or interwoven fiber. By way of example, the mesh material may include PET film, membrane, or screen, such as Dacron®. In other embodiments, the mesh material 712 may be placed on the posterior side 710 of the lead body 702. In such embodiments, the thickness $T_4$ may not include a thickness of the mesh material 712.

As shown in FIGS. 11 and 12, the lead body 702 includes a plurality of windows or holes 715 that extend entirely through the lead body 702. In other embodiments, the windows 715 may extend only partially through the lead body 702 and open to the active side 708. The mesh material 712 extends laterally through the windows 715. The windows 715 are configured to receive a tissue adhesive 782 (FIG. 13) that facilitates securing the NS lead 700 to the nervous tissue.

FIG. 13 illustrates a cross-section of the NS lead 700 in an operable position within a patient. The NS lead 700 is positioned within a head 760 that includes bone 762 of a cranium, a dura mater 764, and a cortex 766 having a cortical surface 768. The cortical surface 768 defines sulci 771-772 and gyri 774-776. The cortical surface 768 includes a target site 780 that is configured to receive electrical energy from the NS lead 700. The NS lead 700 is positioned in a subdural manner such that the NS lead 700 is positioned between the dura mater 764 and the cortical surface 768. In other embodiments, the NS lead 700 may be positioned in an epidural manner along an exterior of the dura mater 764. As shown, the active side 708 of the NS lead 700 directly engages and effectively interfaces with the cortical surface 768 at the target site 780. In some embodiments, the NS lead 700 may be secured to the dura mater 764 using sutures 765.

As shown, the lead body 702 conforms to the non-planar contour of the cortical surface 768. More specifically, the thickness $T_4$ (FIG. 12) and the flexible materials that comprise the lead body 702 permit the lead body 702 to substantially conform to the contour of the cortical surface 768. In some embodiments, after the NS lead 700 is positioned to effectively interface with the cortical surface 768, a tissue adhesive 782 may be deposited within the windows 715. The mesh material 712 may permit the tissue adhesive 782 to flow through the window 715 to the cortical surface 768. When the tissue adhesive 782 sets or sets, the tissue adhesive 782 may effectively secure the mesh material 712 to the cortical surface 768 thereby reducing a likelihood of migration. By way of example, the tissue adhesive may be cyanoacrylate, but other tissue adhesives may be used. In some embodiments, the tissue adhesive 782 may not adhere to the polymer material of the lead body 702. In other embodiments, however, the tissue adhesive 782 may adhere to each of the primary material of the lead body 702, the mesh material 712, and the cortical surface 768.

Figure 14:
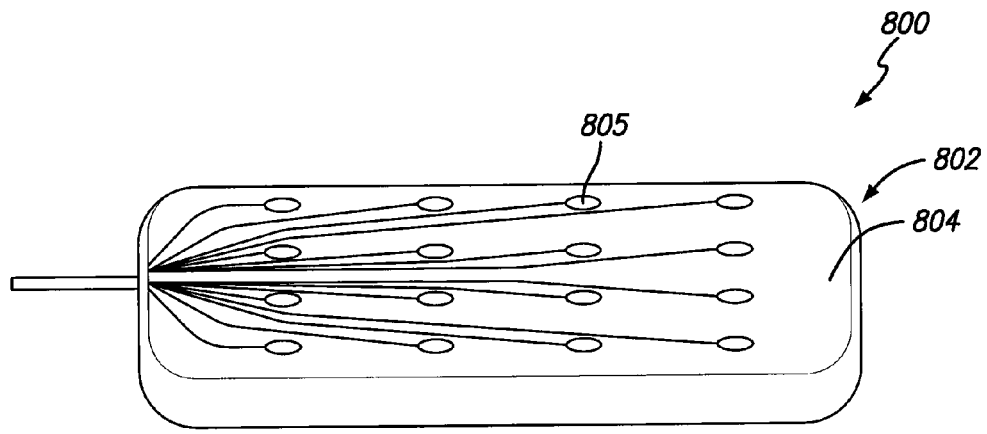
FIG. 14 is a perspective view of a NS lead formed in accordance with an embodiment.

FIG. 14 is a perspective view of a NS lead 800 formed in accordance with an embodiment, which may be used with the NS system 100 (FIG. 1) and may have features that are similar to the other NS leads described herein. The NS lead 800 includes a lead body 802 having an outer casing or covering 804. The NS lead 800 also includes electrodes 805 that are configured to provide NS therapy as described herein.

Figure 15:
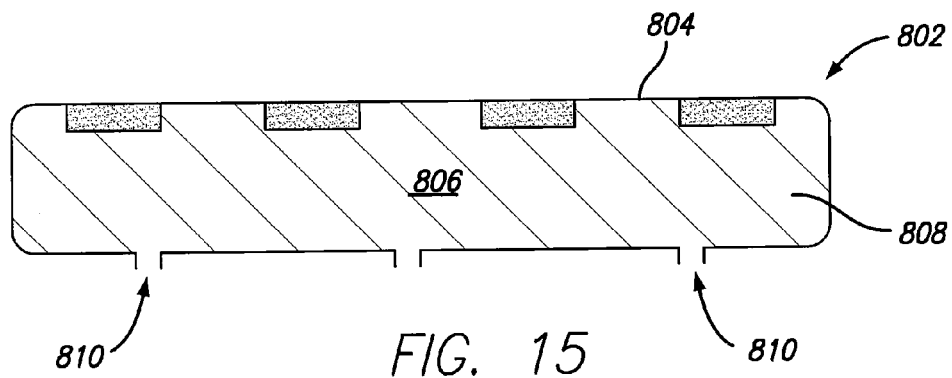
FIG. 15 is a cross-section of the NS lead of FIG. 14.

FIG. 15 illustrates a cross-section of the NS lead 800. As shown, the outer casing 804 surrounds an interior cavity 806 that is at least partially filled with a compressible or pliant material 808. In such embodiments, the outer casing 804 is permitted to conform to a surface of the nervous tissue and permit the electrodes 805 to move with respect to one another and the nervous tissue. As shown, the outer casing 804 may also include ports 810.

In some embodiments, the compressible material 808 may be sponge-like or pillow-like. By way of example, the compressible material 808 may include a visoelastic (e.g., polyurethane) foam or memory foam. When the lead body 802 is pressed against the nervous tissue, such as during surgery, the ports 810 may permit gases within the interior cavity 806 to exit therethrough to permit the lead body 802 to reduce in size and conform to a contour of the nervous tissue. Although not shown, the ports 810 may be covered (e.g., with a cap) to prevent air from drawing back into the interior cavity 806.

In other embodiments, the outer casing 804 may be similar to a bladder in which the compressible material 808 is a solution (e.g., saline). The interior cavity 806 may be partially filled with the solution thereby permitting the outer casing 804 to conform to the contour of the nervous tissue during surgery. In some cases, the ports 810 may be operably coupled to tubes (not shown) that permit the solution to flow into and out of the interior cavity 806 thereby permitting one to adjust a volume of the interior cavity 806.

Figure 16:
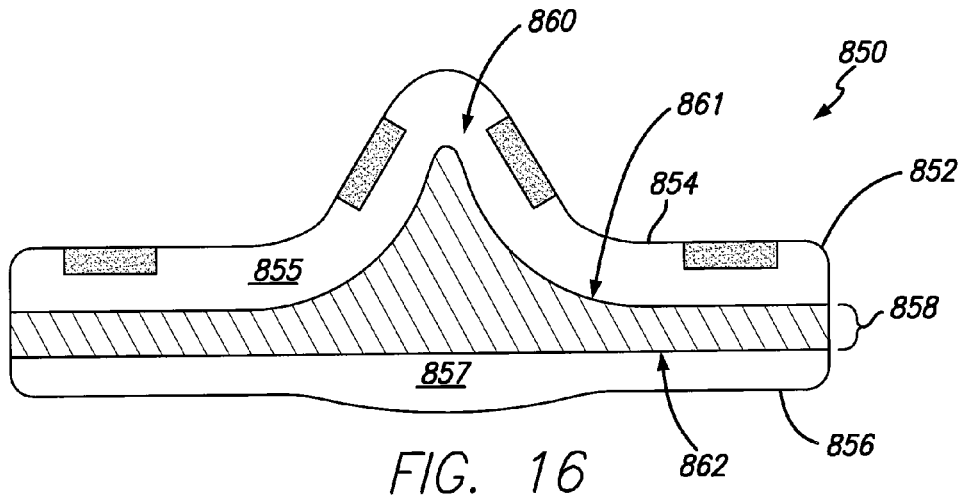
FIG. 16 is a cross-section of a NS lead formed in accordance with an embodiment.

FIG. 16 is a cross-section of a NS lead 850 formed in accordance with an embodiment. The NS lead 850 may include features that are similar to the features of the NS lead 800. For example, the NS lead 850 includes a lead body 852 that includes outer casings 854, 856 and a base layer 858. The outer casings 854, 856 have respective interior cavities 855, 857 and may include a compressible material. The base layer 858 may comprise a material that is more rigid than the compressible material. The base layer 858 may enhance a structural integrity of the NS lead 850.

The base layer 858 includes opposite first and second side 861, 862. As shown, the base layer 858 is shaped to include an internal morphological feature 860 along the first side 861. The interior cavity 855 extends along the first side 861 and about the morphological feature 860. The second side 862 is substantially planar. The interior cavity 857 extends along the second side 862. Like other morphological features described above, the morphological feature 860 may be configured to extend into a depression (e.g., sulcus) along the nervous tissue. As such, the electrodes 805A, 805B may be configured to extend into the depression. However, the compressible material within the interior cavity 855 may enable the outer casing 854 to conform to the contour of the nervous tissue within the depression and permit the electrodes 805A, 805B to move with respect to each other and the nervous tissue. Likewise, the compressible material within the interior cavity 857 may enable the outer casing 856 to conform to a surface of another anatomical body, such as bone or tissue.

Figure 17:
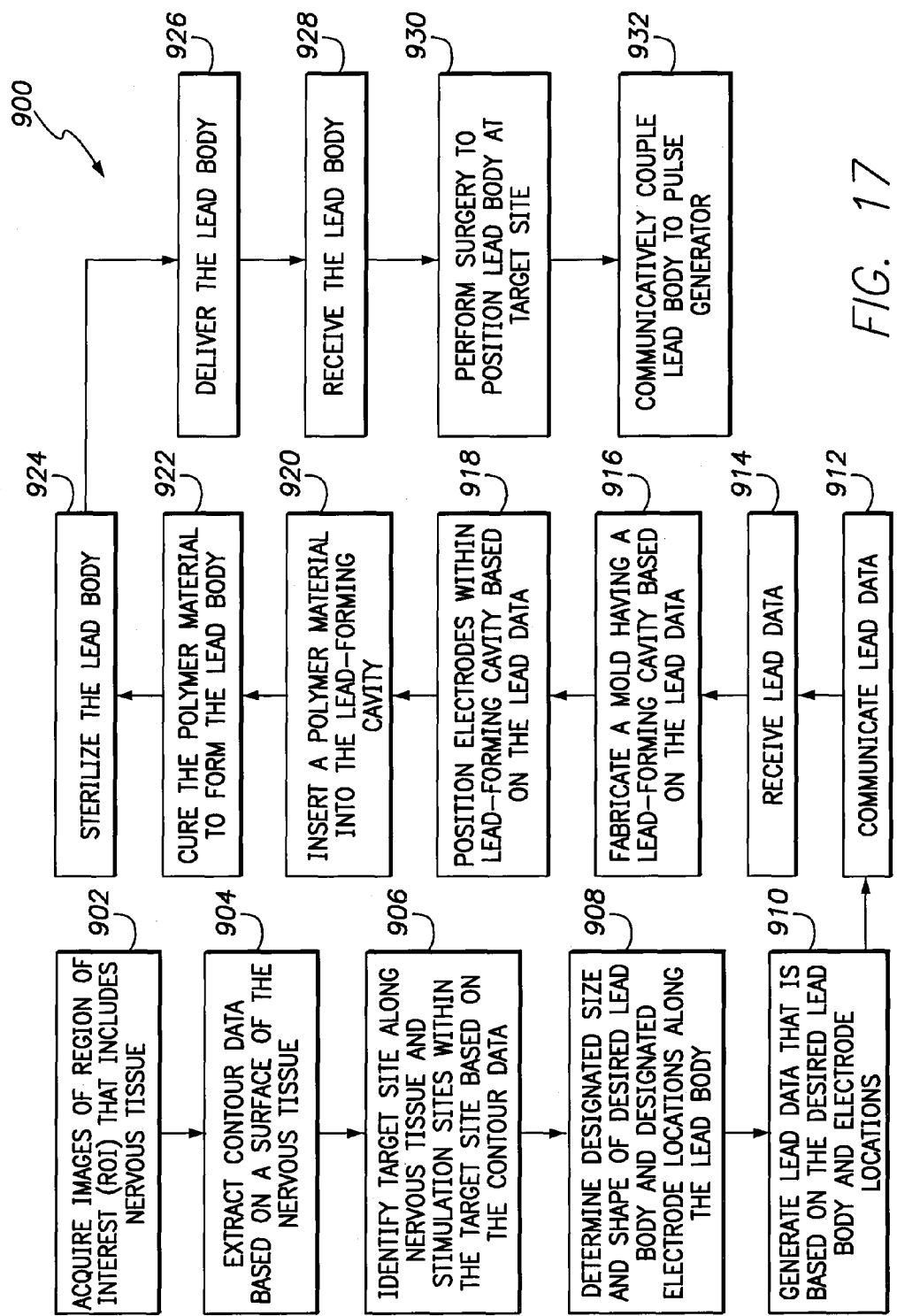
FIG. 17 is a flow chart illustrating a method in accordance with an embodiment.

FIG. 17 is a flow chart illustrating a method 900 in accordance with an embodiment. The method 900, for example, may employ structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion.

In some embodiments, the method 900 may include acquiring (at 902) images of a region of interest (ROI) of a patient that includes nervous tissue. The ROI may be within or include, for example, a head, neck, or back of a patient. The nervous tissue may have a surface that is non-planar. For instance, the tissue surface may include depressions (e.g., gaps, fissures, etc.), projections (ridges, plateaus, peaks, etc.), and the like. By way of example, the nervous tissue may include a brain (e.g., cortex), spinal cord, or a peripheral nerve. Various imaging modalities may be used to acquire the images. For example, the imaging modalities may include magnetic resonance (MR), functional magnetic resonance imaging (fMRI), computed tomography (CT), ultrasound, positron emission tomography (PET), single photon emission computed tomography (SPECT), x-ray, and the like. In particular embodiments, the images are MR images.

The method 900 may also include extracting or rendering (at 904) contour data of the nervous tissue from the images. The contour data may indicate a contour or shape of the nervous tissue. In particular embodiments, the contour data indicates a contour or shape of a surface of the nervous tissue. In addition to the nervous tissue, the contour data may include a contour or shape of nearby structures. By way of one example, the contour data extracted from MR images of a brain may include a contour of the cortical surface, a contour of the dura mater, and/or a contour of bone. Extracting (at 904) may be achieved using one or more algorithms. Exemplary algorithms for extracting contour data have been described in T. Wang et al., "A co-registration approach for electrocorticogram electrode localization using post-implantation MRI and CT of the head," in Proc. 6th Ann. Int'l IEEE EMBS Neural Eng. Conf., 2013; Matsumoto S. et al., "A fast way to visualize the brain surface with volume rendering of MRI data," J Digit Imaging. 1999 November; 12(4):185-90; and Medical Imaging Systems Technology: Methods in cardiovascular and brain systems, edited by Cornelius T. Leondes, World Scientific, (2005) and in particular, Chapters 7, 9, and 10. The extracting (at 904) may generate the contour data.

At 906, a target site for applying NS therapy may be identified. The target site may be automatically determined and/or determined by a doctor(s) or other suitable individuals. Stimulation sites within the target site may also be identified. The identifying (at 906) may be based on, in part, the contour data and a history of the patient. In some embodiments, the identifying (at 906) includes determining a desired coverage of the nervous tissue. For example, based on a history of the patient and the contour data, a doctor or other suitable individual may determine that the NS lead should cover a designated area of the cortical surface. In some embodiments, the identifying (at 906) also includes determining a number of stimulation sites and locations of the stimulation sites along the surface.

The method also includes determining (at 908) a designated size and shape of a desired lead body, including locations of electrodes along the lead body. The desired lead body may include an active side that is configured to complement the nervous tissue. More specifically, the determining (at 908) may include determining a contour of an active surface of the active side. If the nervous tissue has a non-planer contour, the determining (at 908) may include determining a size and shape of one or more morphological features along the active surface of the lead body. The size and shape of the desired lead body may be similar to, for example, the lead bodies 202, 302, 402, 502, and 602 described herein. The contour of the active surface may be similar to, for example, the active surfaces 209, 309, 409, 509, and 609 described herein.

The contour of the active surface may be based on the contour data. The active surface may have a similar shape that complements the non-planer contour of the nervous tissue. As used herein, the term "complement" and the term "similar" does not require that the active surface precisely match the contour of the nervous tissue. For example, the morphological features may not entirely fill a depression of the nervous tissue. Instead, the morphological features may extend only partially into the depression. Nonetheless, the active surface may have a shape that impedes movement of the lead body along the nervous tissue and/or positions the electrodes in intimate contact with the nervous tissue. The locations of the electrodes may be based on the locations of the stimulation sites. More specifically, the electrodes may be located so that, when the lead body is positioned along the nervous tissue, the electrodes are capable of providing electrical fields that stimulate the stimulation sites.

The method 900 may also include generating (at 910) lead data that is based on the designated size and shape of the desired lead body and the designated locations of the electrodes. More specifically, the lead data may include a contour of the active surface and the electrode locations in which the electrodes have different elevations. At 912, the lead data may be communicated to, for example, a party (e.g., manufacturer) responsible for manufacturing the desired lead body. At 914, the lead data is received by the entity.

Figure 18:
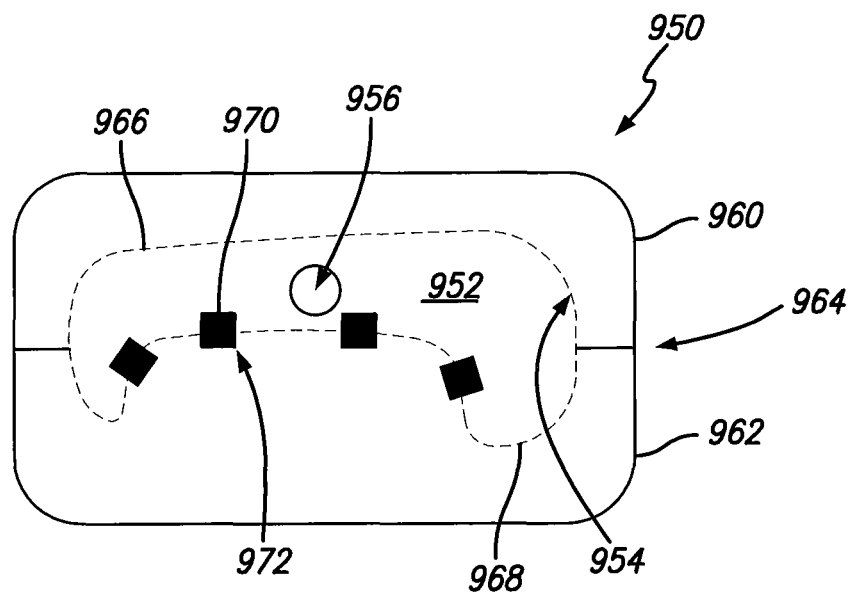
FIG. 18 is an end view of a mold that may be used during the method of FIG. 17.
Figure 19:
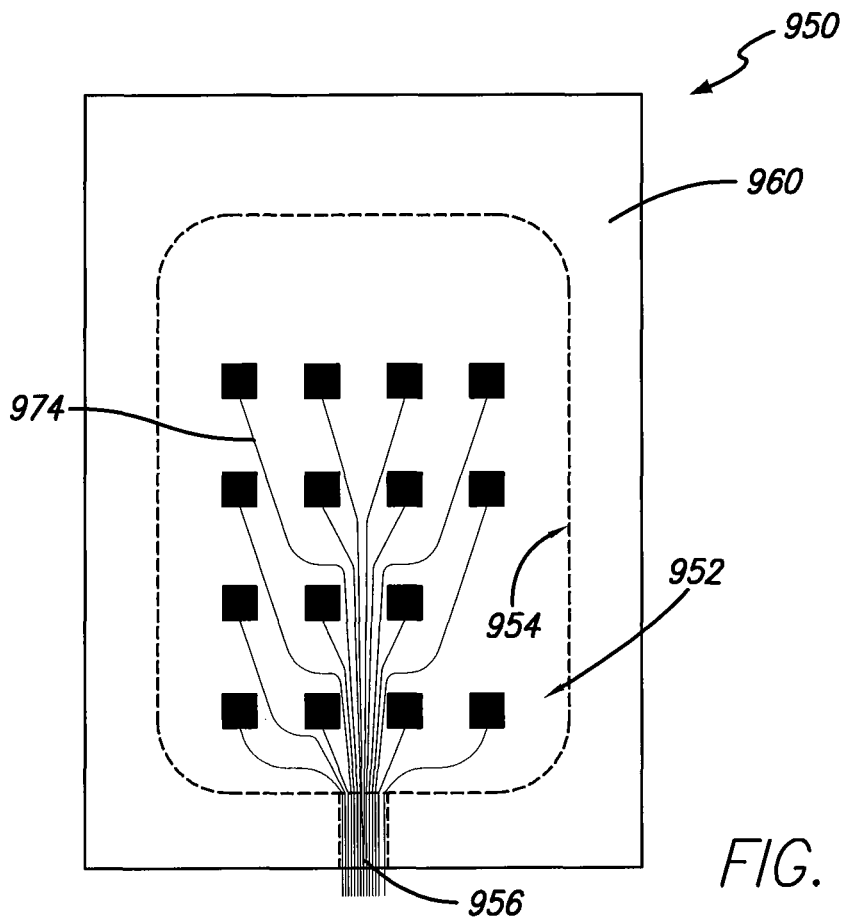
FIG. 19 is a plan view of the mold of FIG. 18 illustrating a lead-forming cavity in phantom.

At 916, a mold may be fabricated that has a lead-forming cavity. For example, FIG. 18 illustrates an end view of a mold 950 having a lead-forming cavity 952, and FIG. 19 illustrates a plan view of the mold 950 in which the lead-forming cavity 952 is indicated in phantom. The lead-forming cavity 952 is defined by an interior surface 954 and has a port 956 that provides access to the lead-forming cavity 952. In some embodiments, the mold 950 may be fabricated through 3D printing. However, it is understood that other methods of fabricating a mold may be used. For example, in some embodiments, the mold 950 may include a pliable internal casing that includes the interior surface 954 and is capable of being re-shaped for manufacturing different lead bodies.

The dimensions of the mold 950, including a contour of the interior surface 954, may be based on the lead data. More specifically, the interior surface 954 may correspond to a negative of the desired lead body. As shown, the mold 950 may include first and second shells 960 (FIG. 18), 962 that interface each other along a seam 964. The first shell 960 may include a first interior portion 966 (FIG. 18) of the interior surface 954, ad the second shell 962 may include a second interior portion 968 (FIG. 18) of the interior surface 954. When the first and second shells 960, 962 are joined together along the seam 964, the first and second interior portions 966, 968 define the lead-forming cavity 952 having the port 956. In some embodiments, the port 956 is sized and shaped to receive an end of a lead cable (not shown).

At 918 (FIG. 17), the method 900 may include positioning electrodes 970 within the lead-forming cavity 952 at designated positions. The designated positions may be based on the lead data. More specifically, the designated positions are configured so that each electrode effectively interfaces with the target site identified at 906. In some embodiments, the interior surface 954 may include indentations 972 (FIG. 18) that are each sized and shaped to receive a portion of a corresponding electrode 970. The electrodes 970 may be electrically coupled to wire conductors 974 (FIG. 19). The wire conductors may extend to and/or through the port 956.

At 920, the method 900 may include inserting a polymer material into the lead-forming cavity 952. The polymer material may be in a liquid form so that the polymer material may be inserted therein. As described above, the polymer material may include silicone (e.g., silicone rubber), PVC, polyethersulfone, PTFE, polyethylene, polyurethane, polyetherimide, polycarbonate, polysulfone, PEEK, polypropylene, polyimide, and the like. At 922, the polymer material may be cured. The curing at 922 may be activated in a designated manner (e.g., heating) or may be permitted to set (e.g., at room temperature).

Optionally, before or after curing (at 922) the lead body. One or more other modifications may be made. For instance, a mesh material (not shown) may be positioned within the lead-forming cavity. In particular embodiments, the mesh material may be positioned along the interior portion 966. Alternatively, the mesh material may be added to a side of the lead body after the lead body is cured. In some embodiments, the mold may be configured to form windows through the lead body. For example, columns may extend through the lead-forming cavity 952 between the interior portions 966, 968. In other embodiments, a bladder may be positioned along one of the sides. The bladder may or may not include electrodes therein.

With the lead body formed, the lead body may be sterilized at 924 and then delivered to the customer at 926. The customer receives the lead body at 928. In some embodiments, the customer may modify the lead body and/or add other elements to the lead body. At 930, a surgery may be performed to position the NS lead at the target site. For example, the lead body may be positioned at the target site such that the active side mates with the non-planar contour of the nervous tissue. At 932, the NS lead may be communicatively coupled to a pulse generator.

In an embodiment, a NS lead configured to provide NS therapy to nervous tissue is provided. The NS lead includes a lead body having an active side and a posterior side that face in generally opposite directions. The active side has an array of electrodes configured to face the nervous tissue and provide the NS therapy to the nervous tissue. The active side has a non-planar contour that includes a plurality of slopes forming a morphological feature. The morphological feature is one of a projection or a depression that extends along a designated path on the active side.

In an embodiment, a NS lead configured to provide NS therapy to nervous tissue is provided. The NS lead includes a lead body having an active side and a posterior side that face in generally opposite directions. The NS lead also includes an array of electrodes provided on the active side and configured to face the nervous tissue and provide the NS therapy to the nervous tissue. The NS lead also includes a non-planar contour formed in the active side. The non-planar contour includes a plurality of slopes that form a morphological feature. The morphological feature is one of a projection or a depression that extends along a designated path on the active side.

In one aspect, the morphological feature has a cross-sectional shape taken transverse to a centerline of the morphological feature. At least one of the cross-sectional shapes or a direction of the centerline changes as the morphological feature extends along the active side.

In another aspect, the lead body includes at least one body edge that defines a perimeter of the active side. The active side has a substantially continuous surface within the perimeter.

In another aspect, the NS lead is oriented with respect to a longitudinal axis, a lateral axis, and an elevation axis that are mutually perpendicular to each other and intersect each other within the lead body. The longitudinal and lateral axes extend through the lead body between the active and posterior sides. The lead body has a thickness that is measured along the elevation axis between the posterior and active sides. The thickness varies as the lead body extends along at least one of the longitudinal axis or the lateral axis.

In another aspect, the array of the electrodes constitutes a three-dimensional array in which at least two of the electrodes are positioned to have different depths within the nervous tissue.

In another aspect, the morphological feature is a ridge that is sized and shaped to extend into a sulcus of a cortex.

In another aspect, the active side includes an electrode area that includes an entirety of the array of electrodes and the lead body includes a grip portion. The grip portion includes at least a portion of the morphological feature and is void of any of the electrodes.

In another aspect, the active side includes a plurality of the morphological features having respective designated paths that extend in different directions.

In another aspect, at least a portion of the lead body that includes the active side is compressible to permit adjustment of the electrodes relative to one another.

In another aspect, the lead body includes a window that extends entirely through the lead body.

In an embodiment, a method is provided that includes receiving lead data that has a designated size and shape of a desired lead body and designated locations of electrodes along the lead body. The method also includes fabricating a mold based on the lead data. The mold has a lead-forming cavity defined by an interior surface. At least a portion of the interior surface has a non-planar contour. The method includes positioning an array of electrodes within the lead-forming cavity along the interior surface based on the locations in the lead data. The method also includes inserting a polymer material into the lead-forming cavity. The polymer material surrounds the electrodes. The method also includes curing the polymer material to form the lead body. The lead body has an active side with a plurality of slopes forming a morphological feature.

In one aspect, the method includes receiving imaging data of nervous tissue having a tissue surface that includes at least one of a gap or a projection, the lead data being based on the imaging data.

In another aspect, the imaging data includes magnetic resonance (MR) images.

In another aspect, curing the polymer material includes activating the polymer material or permitting the polymer material to set.

In another aspect, the active side includes a plurality of the morphological features. The morphological features extend along designated paths, wherein at least two of the morphological features have paths that extend in different directions.

In another aspect, the lead body includes a mesh material and has a plurality of windows extending therethrough. The mesh material extends across the windows.

In an embodiment, a method is provided that includes acquiring images of nervous tissue of a patient. The nervous tissue has a non-planar contour. The method also includes generating lead data based on the images of the nervous tissue. The lead data includes a designated size and shape of a desired lead body and designated locations of electrodes along the lead body. The lead body has an active side that complements the non-planar contour of the nervous tissue. The method also includes communicating the lead data for fabricating the lead body and receiving the lead body after fabrication. The method also includes positioning the lead body at a target site within the patient such that the active side mates with the non-planar contour of the nervous tissue.

In one aspect, the images include magnetic resonance (MR) images.

In another aspect, a surface of the nervous tissue is a cortical surface of a brain. In some embodiments, positioning the lead body at the target site includes at least one of positioning a ridge of the active side within a sulcus of the cortical surface or positioning a valley of the active side along a gyrus of the cortical surface.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings. Also, it is to be understood that phraseology and terminology used herein with reference to device or element orientation (such as, for example, terms like "central," "upper," "lower," "front," "rear," "distal," "proximal," and the like) are only used to simplify description of one or more embodiments described herein, and do not alone indicate or imply that the device or element referred to must have a particular orientation. In addition, terms such as "outer" and "inner" are used herein for purposes of description and are not intended to indicate or imply relative importance or significance.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the presently described subject matter without departing from its scope. While the dimensions, types of materials and coatings described herein are intended to define the parameters of the disclosed subject matter, they are by no means limiting and are exemplary embodiments. Many other embodiments will be apparent to those of skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112(f), unless and until such claim limitations expressly use the phrase "means for" followed by a statement of function void of further structure.

The following claims recite aspects of certain embodiments of the inventive subject matter and are considered to be part of the above disclosure.

What is claimed is:

1. A neurostimulation (NS) lead configured to provide NS therapy to nervous tissue, the NS lead comprising:
    a lead body having a first edge and a second edge, the lead body having an active side and a posterior side that face in generally opposite directions;
    an array of electrodes provided on the active side and configured to face the nervous tissue and provide the NS therapy to the nervous tissue;
    the active side of the lead body having a first planar portion at the first edge and a second planar portion at the second edge; and
    a non-planar contour formed in the active side, the non-planar contour including a plurality of slopes that form a morphological feature, the morphological feature being one of a projection or a depression that extends along a designated path on the active side intermediate the first planar portion and the second planar portion; and
    a first electrode of the array of electrodes positioned on the first planar portion and a second electrode of the array of electrodes positioned on one of the plurality of slopes of the non-planar contour.

2. The NS lead of claim 1, wherein the morphological feature has a cross-sectional shape taken transverse to a centerline of the morphological feature, at least one of the cross-sectional shape or a direction of the centerline changing as the morphological feature extends along the active side.

3. The NS lead of claim 1, wherein the lead body includes at least one body edge that defines a perimeter of the active side, the active side having a substantially continuous surface within the perimeter.

4. The NS lead of claim 1, wherein the NS lead is oriented with respect to a longitudinal axis, a lateral axis, and an elevation axis that are mutually perpendicular to each other and intersect each other within the lead body, the longitudinal and lateral axes extending through the lead body between the active and posterior sides, wherein the lead body has a thickness that is measured along the elevation axis between the posterior and active sides, the thickness varying as the lead body extends along at least one of the longitudinal axis or the lateral axis.

5. The NS lead of claim 1, wherein the array of the electrodes constitutes a three-dimensional array in which at least two of the electrodes are positioned to have different depths within the nervous tissue.

6. The NS lead of claim 1, wherein the morphological feature is a ridge that is sized and shaped to extend into a sulcus of a cortex.

7. The NS lead of claim 1, wherein the active side includes an electrode area that includes an entirety of the array of electrodes and the lead body includes a grip portion, the grip portion including at least a portion of the morphological feature and being void of any of the electrodes.

8. The NS lead of claim 1, wherein the active side includes a plurality of the morphological features having respective designated paths that extend in different directions.

9. The NS lead of claim 1, wherein at least a portion of the lead body that includes the active side is compressible to permit adjustment of the electrodes relative to one another.

10. The NS lead of claim 1, wherein the lead body includes a window that extends entirely through the lead body.

* * * * *